(12) United States Patent
Gokel et al.

(10) Patent No.: US 10,548,319 B2
(45) Date of Patent: Feb. 4, 2020

(54) COMPOSITIONS AND METHODS FOR SYNTHETIC AMPHIPHILE-INDUCED CHANGES IN PLANT ROOT MORPHOLOGY

(71) Applicant: The Curators of the University of Missouri, Columbia, MO (US)

(72) Inventors: George W. Gokel, Chesterfield, MO (US); Mohit B. Patel, St. Louis, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 15/502,449

(22) PCT Filed: Aug. 7, 2015

(86) PCT No.: PCT/US2015/044353
§ 371 (c)(1),
(2) Date: Feb. 7, 2017

(87) PCT Pub. No.: WO2016/022991
PCT Pub. Date: Feb. 11, 2016

(65) Prior Publication Data
US 2018/0077933 A1    Mar. 22, 2018

Related U.S. Application Data

(60) Provisional application No. 61/999,852, filed on Aug. 7, 2014, provisional application No. 62/154,934, filed on Apr. 30, 2015.

(51) Int. Cl.
*A01N 43/72*  (2006.01)

(52) U.S. Cl.
CPC .................................. *A01N 43/72* (2013.01)

(58) Field of Classification Search
None
See application file for complete search history.

(56) References Cited

FOREIGN PATENT DOCUMENTS

| WO | 2008062035 | A2 | 5/2008 |
| WO | 2013104026 | A1 | 7/2013 |
| WO | 2014049546 | A2 | 4/2014 |

OTHER PUBLICATIONS

Yannnitz, Carl R., and George W. Gokel. "Synthetic, biologically active amphiphilic peptides." Chemistry & biodiversity 4.6 (2007) 1395-1412.*

Gatto, Vincent J., et al. "Syntheses and binding properties of bibrachial lariat ethers (BiBLEs): survey of synthetic methods and cation selectivities." The Journal of Organic Chemistry 51.26 (1986): 5373-5384.*
Wang, Min, et al. "The critical role of potassium in plant stress response." International journal of molecular sciences 14.4 (2013): 7370-7390.*
Ebrahimi, Sattar. "Synthesis of novel bibrachial lariat ethers (BiBLEs) containing [1, 2, 4] triazolo [3, 4-b][1, 3, 4] thiadiazines." South African Journal of Chemistry 66 (2013): 77-79.*
Abbas et al. "Antagonistic interaction between auxins and the growth regulator NC 9634," Plant Growth Regulation, 1984, pp. 3-8, vol. 2.
Cook et al. "NMR Structure and Dynamic Studies of an Anion-Binding, Channel-Forming Heptapeptide," Journal American Chemical Society, 2006, pp. 1633-1638, vol. 128.
Doerner, Peter, "Plant Roots: Recycled Auxin Energizes Patterning and Growth," Current Biology, 2007, pp. R72-R73, vol. 18, No. 2.
Gamborg et al., "Plant Tissue Culture Media," In Vitro, 1976, pp. 473-478, vol. 12, No. 7.
Haughn et al., "Sulfonylurea-resistant mutants of *Arabidopsis thaliana*," Mol Gen Genet, 1986, pp. 430-434, vol. 204.
Macklon et al., "Effects of some Cyclic 'Crown' Polyethers on Potassium Uptake, Efflux and Transport in Excised Root Segments and Whole Seedlings," Annals of Botany, 1983, pp. 345-356, vol. 52.
Murray et al., "Spacer Chain Length Dependence in Hydraphile Channels: Implications for Channel Position Within Phospholipid Bilayers," J. of Supramolecular Chemistry, 2001, pp. 23-30, vol. 1.
Patel et al., "Hydraphile synthetic ion channels alter root architecture in *Arabidopsis thaliana*," Chem. Commun., 2014, pp. 11562-11564, vol. 50.
Sibbett et al., "Olive Spray Thinning Guidelines," University of California, Division of Agriculture and Natural resources, 2006, Publication 7238 (formerly 2475), pp. 1-3, retreived from the internet:<http://danrcs.ucdavis.edu/.
Weber et al., "Dynamic Assessment of Bilayer Thickness by Varying Phospholipid and Hydraphile Synthetic Channel Chain Lengths," J. Am Chem Soc., 2005, pp. 636-642, vol. 127, No. 2.
International Search Report and Written Opinion dated Nov. 6, 2015 of corresponding International Application PCT/US2015/044353, 8 pages dated.

\* cited by examiner

*Primary Examiner* — John Pak
*Assistant Examiner* — Daniel L Branson
(74) *Attorney, Agent, or Firm* — Thompson Coburn LLP; William A. Holtz

(57) ABSTRACT

The disclosure provides a method for increasing the lateral root development of a plant by exposing said plant to a composition containing a synthetic amphiphile. By increasing the number of lateral roots, the surface area of the root structure is increased, making the plants better able to survive such stresses as drought or low nutrients.

4 Claims, 13 Drawing Sheets

COMPOSITIONS AND METHODS FOR SYNTHETIC AMPHIPHILE-INDUCED CHANGES IN PLANT ROOT MORPHOLOGY

CROSS-REFERENCE TO RELATED APPLICATIONS

This application is a 35 U.S.C. § 371 National Phase Application of International Patent Application No. PCT/US2015/044353, filed Aug. 7, 2015, claiming the benefit of U.S. Ser. No. 61/999,852 filed Aug. 7, 2014 and U.S. Ser. No. 62/154,934 filed Apr. 30, 2015, all of which are incorporated by reference herein in their entireties.

STATEMENT OF FEDERALLY SPONSORED RESEARCH

This invention was made with Government support under Grant No. CHE 1307324 awarded by the National Science Foundation. The Government has certain rights in the invention.

BACKGROUND

The present disclosure relates to methods for inducing changes in plant root morphology. For example, certain methods are directed to increasing the development of lateral root growth while decreasing the development of primary roots.

Natural protein channels function in many organisms to facilitate the transport of ions across cellular boundaries. Channels are known to play critical roles in bacteria, in fungi, in mammalian cells, and in plants. The cells of each of these organisms are bounded by a barrier membrane or cell wall but the nature of these boundary layers can be dramatically different. Even in simple organisms such as bacteria, the boundary layers of Gram-positive and Gram-negative bacteria are very different and a further variation occurs in Mycobacteria. The difference between the boundary layers of mammals and plants is even more dramatic.

A similarity among all of these cell types is the need for various molecular and ionic species to pass through the membranes so that ionic balance can be maintained, so that nutrients can enter, and so waste products can exit. Plants in particular have a cell wall that creates challenges in terms of penetration. Natural protein channels typically mediate this process.

Hydraphiles are synthetic amphiphiles that emulate channel function in bacteria. At certain concentrations, they are toxic to bacteria, by a mechanism that disrupts ion homeostasis. Recently, it was shown that hydraphiles enhance the efficacy of antibiotic function against bacteria when co-administered with appropriate pharmaceuticals.

It has been reported that benzo-15-crown-5 transports $K^+$ ions in wheat roots at low concentrations (Huang, D., Wang, D., Fu. T., Que, R., Zhang, J., Huang, L., Zhang, Z.; *Journal of Nanjing University of Natural Science* 1980, 2, 33-44). In other work, it was found that benzo-18-crown-6 reduced potassium efflux, transport, and uptake in onion root segments as reported in Macklon, A. E. S., Sim, A., Parsons, D. G., Truter, M. R., Wingield, J. N.; Effects of some Cyclic 'Crown' Polyethers on Potassium Uptake, Efflux and Transport in Excised Root Segments and Whole Seedlings. *Annals of Botany* 1983, 52(3), 345-356.

SUMMARY

Certain embodiments provide for methods of treating a plant by adding synthetic amphiphiles to a plant's growth media at defined concentrations. In certain embodiments, treatment at certain concentrations results in changes in plant root morphology, such as decreased primary root length and/or increased lateral root density. In certain embodiments, such as at higher concentrations, treatment inhibits the growth of the plant.

Certain embodiments are drawn to methods for altering the root morphology of a plant comprising treating one or more plants with a composition comprising a synthetic amphiphile. In certain embodiments, the plant is grown on a solid plant growth media that comprises the synthetic amphiphile. In certain other embodiments, the plant is supplemented with an aqueous solution that comprises the synthetic amphiphile. In certain embodiments, the plant is contacted with the aqueous solution. In certain embodiments, the plant is contacted with the aqueous solution on its roots. In certain embodiments, the alteration in the plant root morphology is a decrease in the primary root length, an increase in the lateral root density of the plant, or both a decrease in the primary root length and an increase in the lateral root density, compared to the average primary root length and/or lateral root density of a statistically significant control population of plants that has not been treated with a synthetic amphiphile. In certain embodiments, the treated plant exhibits at least a 2-fold, 3-fold, 4-fold, 5-fold, or more increase in lateral root density compared to the average lateral root density of a statistically significant control population that has not been treated with the synthetic amphiphile. In certain embodiments, a treated plant is selected based on the alteration in root morphology. In certain embodiments, the treated plant is selected for an increase in the lateral root density of the plant or selected for both an increase in the lateral root density and a decrease in the primary root length. In certain embodiments, the treated plant is selected for at least a 2-fold, 3-fold, 4-fold, 5-fold, or more increase in lateral root density. In certain embodiments, the method further comprises growing a selected plant following its selection.

In certain embodiments, the amount of the synthetic amphiphile is an amount that is lower than the amount at which a toxic effect is apparent for certain plants. For example, in certain embodiments, the concentration of the synthetic amphiphile in the composition is less than about 50 µM. For example, the concentration of the synthetic amphiphile in the composition is from about 1.0 µM to about 50 µM, or from about 0.1 µM to about 50 µM, or from about 0.01 µM to about 50 µM, or from about 0.001 µM to about 50 µM. For example, the concentration of synthetic amphiphile in the composition is less than about 25 µM. For example, the concentration of the synthetic amphiphile in the composition is from about 1.0 µM to about 25 µM, or from about 0.1 µM to about 25 µM, or from about 0.01 µM to about 25 µM, or from about 0.001 µM to about 25 µM.

In certain embodiments, the amount of synthetic amphiphile is an amount that is higher than the amount at which a toxic effect is apparent for certain plants. For example, the concentration of the synthetic amphiphile in the composition is greater than about 25 µM. For example, the concentration of the synthetic amphiphile in the composition is greater than about 50 µM. For example, the concentration of the synthetic amphiphile in the composition is greater than about 75 µM. For example, the concentration of the synthetic amphiphile in the composition is from about 25 µM to about 100 µM. For example, the concentration of the synthetic amphiphile in the composition is from about 50 µM to about 100 µM. For example, the concentration of the synthetic amphiphile in the composition is from about 25 µM to about 75 μM. For example, the concentration of the synthetic amphiphile in the composition is from about 50 μM to about 75 μM. For example, the concentration of the synthetic amphiphile in the composition is from about 75 μM to about 100 μM.

In certain embodiments, the primary root length is decreased by at least 90% compared to the average primary root length of a statistically significant control population that has not been treated with the synthetic amphiphile. In certain embodiments, the plant with altered root morphology is a crop plant and wherein the plant exhibits increased yield compared to the average yield of a statistically significant control population that has not been treated with the synthetic amphiphile. In certain embodiments, the plant with altered root morphology exhibits improved growth in low nutrient growth conditions compared to the average growth of a statistically significant control population that has not been treated with the synthetic amphiphile. In certain embodiments, the plant with altered root morphology exhibits improved tolerance to stress conditions selected from the group consisting of drought, flooding, high salt growth conditions, extreme cold, and extreme heat, compared to the average tolerance of a statistically significant control population that has not been treated with the synthetic amphiphile.

Certain embodiments are drawn to methods for inhibiting plant growth comprising treating one or more plants with a composition comprising a synthetic amphiphile at a concentration higher than the concentration that increases lateral root density and decreases primary root length. In certain embodiments, the plant is contacted with the composition on its roots, stems, and/or leaves. In certain embodiments, the plant is contacted with the composition on its leaves. For example, in certain embodiments the concentration of the synthetic amphiphile in the composition is greater than about 25 μM. For example, in certain embodiments the concentration of the synthetic amphiphile in the composition is greater than about 50 μM. For example, in certain embodiments the concentration of the synthetic amphiphile in the composition is greater than about 75 μM. For example, in certain embodiments the concentration of the synthetic amphiphile in the composition is from about 25 μM to about 100 μM or from about 50 μM to about 100 μM or from about 75 μM to about 100 μM. For example, in certain embodiments the concentration of the synthetic amphiphile in the composition is from about 25 μM to about 75 μM or from about 50 μM to about 75 μM.

In certain embodiments, the synthetic amphiphile comprises a hydraphile structure of Formula I:

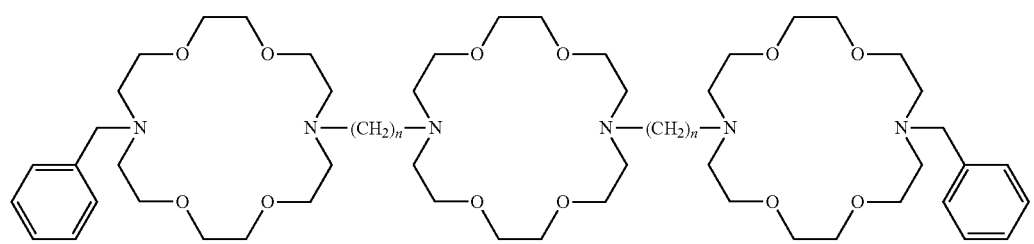

$n = 8, 10, 12, 14, 16, 18$ and $20$ wherein n is 8, 10, 12, 14, 16, 18, or 20. In certain embodiments, n is 14 or 16.

In certain embodiments, the synthetic amphiphile comprises a lariat ether structure of Formula II:

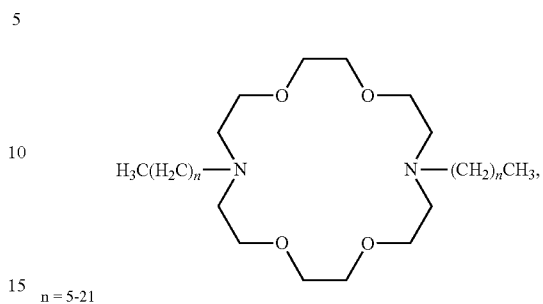

$n = 5-21$ wherein n is 5 to 21. In certain embodiments, n is 7 or 9.

In certain embodiments, the synthetic amphiphile comprises a lariat ether amide structure of Formula III:

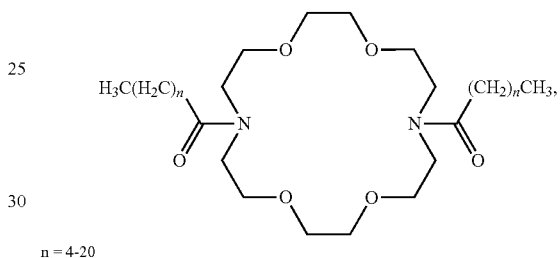

$n = 4-20$ wherein n is 4 to 20.

In certain embodiments, the synthetic amphiphile comprises a peptide-based synthetic amphiphile structure of Formula IV:

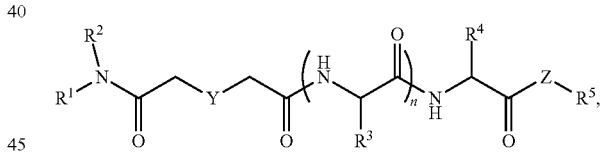

wherein:
$R^1$ and $R^2$ are straight-chained, branched-chained, cyclic alkyl, aralkyl, or substituted or unsubstituted aryl having from 1-24 carbons and $R^1$ and $R^2$ can be the same or different;

$R^3$ represents the side chains of amino acids in a peptide sequence having 4-10 amino acids, which can be the same or different;

$R^4$ is the side chain of an amino acid that is the C-terminal amino acid;

$R^5$ is a straight-chained, branched-chained, cyclic alkyl, aralkyl, or substituted or unsubstituted aryl having from 1-18 carbons;

Y is substituted or unsubstituted carbon, nitrogen, sulfur, oxygen or absent;

Z is the connecting element between the C-terminal amino acid and the element defined by $R^5$, typically, O, N, or S; and n is an integer from 3-10.

In certain embodiments, the synthetic amphiphile comprises a peptide-based synthetic amphiphile structure of Formula V:

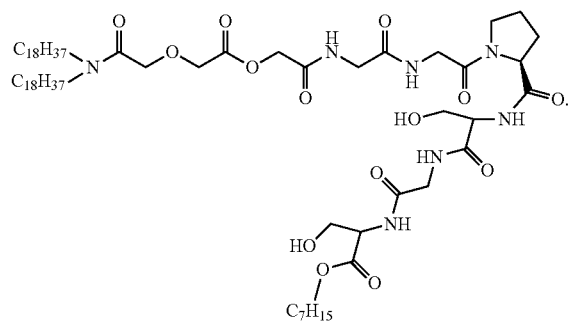

In certain embodiments, methods comprise supplementing a plant with a growth medium comprising a synthetic hydraphile having Formula I:

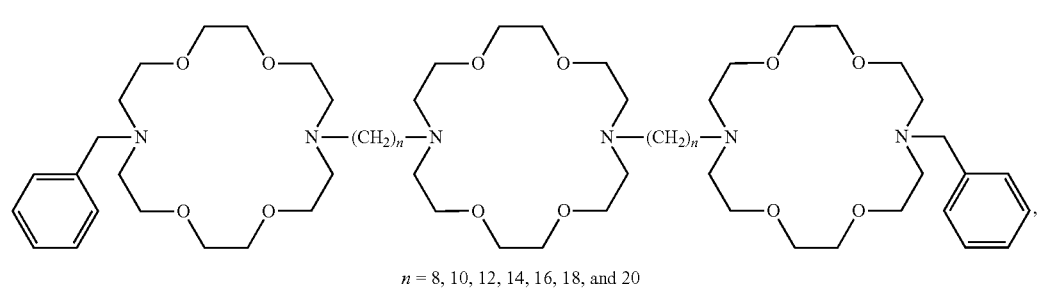

wherein n can be 8, 10, 12, 14, 16, 18, or 20.

In certain embodiments, methods comprise supplementing a plant with growth medium containing a synthetic lariat ether having Formula II:

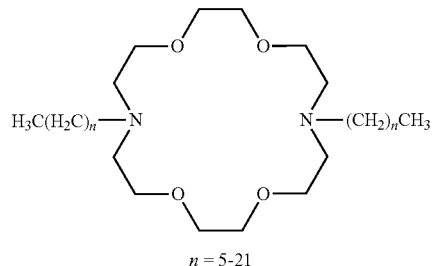

wherein n can be 5 to 21. In certain embodiments, the growth medium can comprise concentrations up to 50 µM or more before toxicity is the predominant effect.

In certain embodiments, methods comprise supplementing a plant with growth medium containing a synthetic lariat ether amide having Formula III:

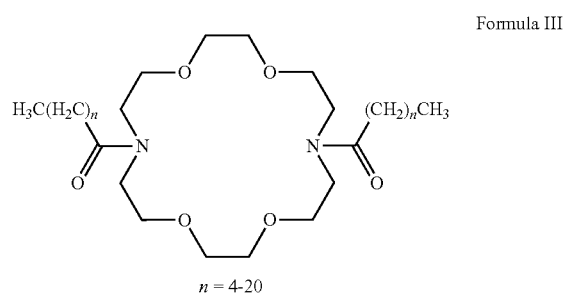

wherein n is 4 to 20 (overall side arm lengths are $C_6$ to $C_{22}$). In certain embodiments, the growth medium can comprise concentrations up to 50 µM or more before toxicity is the predominant effect.

In certain embodiments, methods comprise supplementing a plant with growth medium containing a synthetic anion transporter having Formula IV:

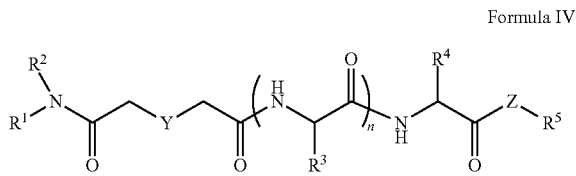

Formula IV

Wherein:
R¹ and R² are straight-chained, branched-chained, cyclic alkyl, aralkyl, or substituted or unsubstituted aryl having from 1-24 carbons and R¹ and R² can be the same or different;
R³ represents the side chains of amino acids in a peptide sequence having 4-10 amino acids, which can be the same or different;
R⁴ is the side chain of an amino acid that is the C-terminal amino acid;
R⁵ is a straight-chained, branched-chained, cyclic alkyl, aralkyl, or substituted or unsubstituted aryl having from 1-18 carbons;
Y is substituted or unsubstituted carbon, nitrogen, sulfur, oxygen, or absent;
Z is the connecting element between the C-terminal amino acid and the element defined by R⁵, typically, O, N, or S; and
n is an integer from 3-10.

In certain embodiments, methods comprise supplementing a plant with growth medium containing a synthetic anion transporter having Formula V:

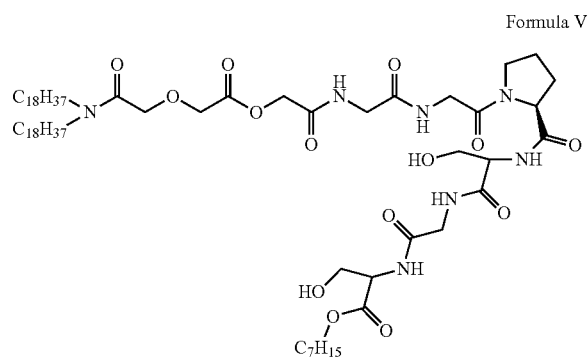

Formula V

DETAILED DESCRIPTION

It is to be noted that the term "a" or "an" entity refers to one or more of that entity; for example, "a hydraphile" is understood to represent one or more hydraphile compounds. As another example, "a synthetic anion transporter" is understood to represent one or more synthetic anion transporter (SAT) compounds. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. Units, prefixes, and symbols are denoted in their Système International de Unites (SI) accepted form. Numeric ranges are inclusive of the numbers defining the range. The headings provided herein are not limitations of the various aspects or aspects of the disclosure, which can be had by reference to the specification as a whole.

Overview.

Disclosed herein are methods for altering root morphology in plants by growing plants in nutrient media containing synthetic amphiphiles. Lateral roots provide a greater surface area for water and nutrient infusion and often develop when a plant is under stress, such as in drought, flooding, high salt growth conditions, extreme cold, and other challenging conditions.

Under normal conditions of temperature, light, moisture, and nutrients, certain plants grow with a single primary root and few, if any, lateral roots. It has been discovered that when the plant is supplemented with a solution or media containing certain concentrations of synthetic amphiphile molecules, a significant change is observed in the root morphology, which alters from a single primary root to multiple lateral roots and a primary root of diminished length.

Figure 1:
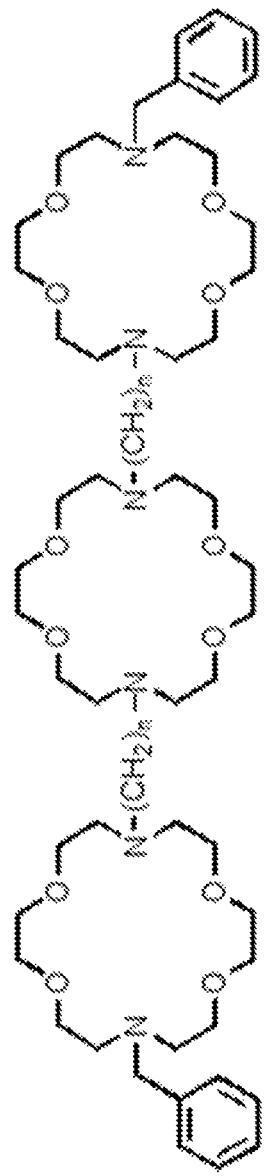
FIG. 1 illustrates the chemical structures of lariat ethers, lariat ether amides, and hydraphiles, which are exemplified in the present disclosure.
Figure 1:
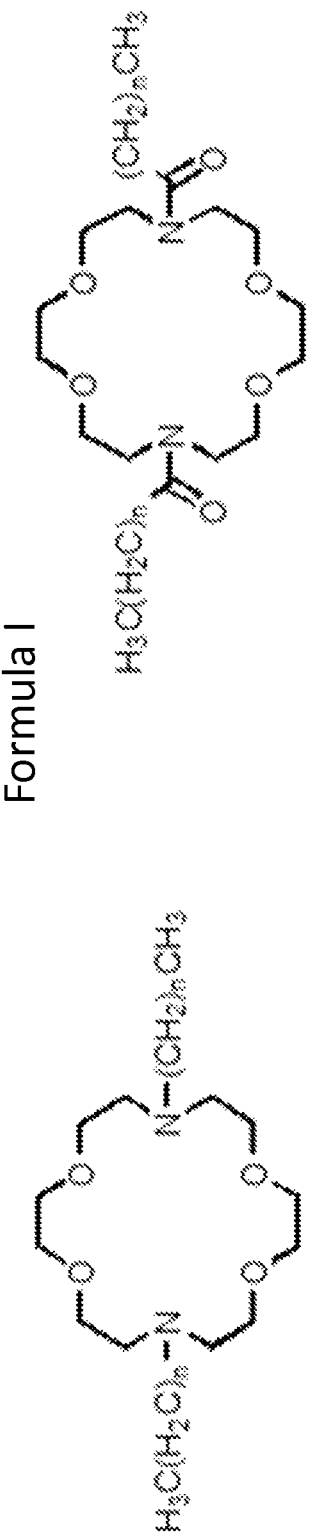

Representative examples of three types of synthetic amphiphiles are: hydraphiles comprising the chemical structure of Formula I; lariat ethers comprising the chemical structure of Formula II; and lariat ether amides comprising the chemical structure of Formula III (FIG. 1). Other representative examples are synthetic anion transporters ("SATs"). Examples of these compounds have been added in the growth media in plant model systems in order to treat the plants with synthetic amphiphiles and resulted in changes in root morphology.

The effect treating a plant with a composition comprising a synthetic amphiphile on root morphology or other physical characteristics or attributes can be quantitated. For example, a change in primary root length can be determined by measuring the difference, if any, in primary root length of a plant treated with the composition compared to the average of a control sample of plants of the same type grown under identical conditions in the absence of the composition. A change in lateral root density can be determined by comparing the lateral root density of a plant treated with the composition to the average lateral root density of a sample grown under identical conditions in the absence of the composition. Lateral root density can be determined by dividing the number of lateral roots by the length of the primary root. In certain embodiments for any quantitated characteristic or attribute, the average value of the control is the average of a statistically significant population of control plants. For example, in certain illustrative embodiments disclosed herein, three trials of about 20 plants each were used to determine the average of the control.

Hydraphiles.

Synthetic amphiphiles known as hydraphiles that contain three macrocyclic polyether rings are known to affect plant root morphology as disclosed in Patel, M. B., Stavri, A., Curvey, N. S., Gokel, G. W.; Hydraphile synthetic ion channels alter root architecture in *Arabidopsis thaliana*. *Chemical Communications*. 2014, 50, 11562-11564. These hydraphiles are compounds that insert into bilayer membranes and form ion-conducting channels.

Certain aspects are drawn to treating a plant by the addition of any one of the synthetic hydraphiles disclosed. In certain embodiments, the plant is supplemented with a composition comprising the hydraphile. In certain embodiments, the plant is contacted with a composition comprising the hydraphile. In certain embodiments, the composition comprising the hydraphile is water and/or an aqueous solution. In certain embodiments, the composition comprising the hydraphile is a solid plant growth medium. An illustrative example is a plant nutrient media containing 0.5% sucrose and 0.6% agar. In certain embodiments, the hydraphile is dissolved, suffused, etc., as appropriate for the composition within which it is contained, which can be readily determined by one of ordinary skill in the art. In certain embodiments, the addition of a hydraphile to a plant causes a change in plant root morphology such as a change in primary root length and/or a change in lateral root density. In certain embodiments, the addition of a hydraphile causes a decrease in primary root length and/or an increase in lateral root density. In certain embodiments, addition inhibits growth of the plant.

Certain illustrative hydraphile embodiments are shown in Table 1. Table 1 shows the effect of three benzyl hydraphiles (of Formula I), compounds 1-3 (having n=8, n=14, and n=16, respectively), on primary root development.

TABLE 1

Additive effects on *A. thaliana* primary root development[a]

| *A. thaliana* (Col-0) plant | Primary root length (mm) | Decrease in primary root length (%) |
|---|---|---|
| Plant nutrient + sucrose (PNS) | 38 ± 4 | 0 |
| DMSO (0.2 vol-%) | 35 ± 3 | 8 |
| $C_8$ hydraphile (1) 20 μM | 34 ± 7 | 9 |
| $C_8$ hydraphile (1) 50 μM | 31 ± 6 | 19 |
| $C_{14}$ hydraphile (2) 20 μM | 14 ± 2 | 63 |
| $C_{14}$ hydraphile (2) 50 μM | 0.7 ± 0.2 | 98 |
| $C_{16}$ hydraphile (3) 10 μM | 23 ± 0.4 | 39 |
| $C_{16}$ hydraphile (3) 20 μM | 15 ± 0.5 | 61 |
| $C_{16}$ hydraphile (3) 50 μM | 4 ± 0.2 | 90 |

[a]The standard deviations reflect a minimum of three trials of 23-27 plants per trial.

The data in Table 1 are expressed as the measured primary root length in millimeters (middle column) and as the percent the primary root length diminished under the specified conditions. Compounds 2 and 3 had a concentration dependent effect on primary root length. In the presence of 20 μM and 50 μM compound 2, the primary root length decreased to 14±2 mm and 0.7±0.2 mm, respectively. The primary root development was decreased by 63% with 20 μM compound 2. When the concentration of compound 2 was increased to 50 μM, the primary root development was completely inhibited; it was decreased by 98%. In the presence of 10 μM and 20 μM $C_{16}$ benzyl hydraphile (compound 3), the primary root length was decreased to 23±0.4 mm and 15±0.5 mm, respectively. In the presence of 50 μM compound 3, the primary root length decreased to 4±0.2 mm, a 90% decrease in root length. Increasing concentrations of compounds 2 and 3 resulted in decreased primary root length of the *A. thaliana* samples studied. Both $C_{14}$ and $C_{16}$ benzyl hydraphiles inhibit the primary root development at 50 μM concentration. Here, the primary root length of the *A. thaliana* plant in presence of 50 μM hydraphile is so short that the growth and development of the plant is minimal and also causes chlorosis of the leaves. This could result in inhibition of plant growth.

Further studies were conducted to determine the effect of benzyl hydraphiles (of Formula I) on the lateral root density of *A. thaliana*. The average number of lateral roots observed for plant nutrient media plus sucrose (PNS) and for PNS in the presence of DMSO control was 5±1. The lateral root density for PNS was 0.14±0.02 and the same for 0.2 volume-% DMSO (0.13±0.01).

Figure 2:
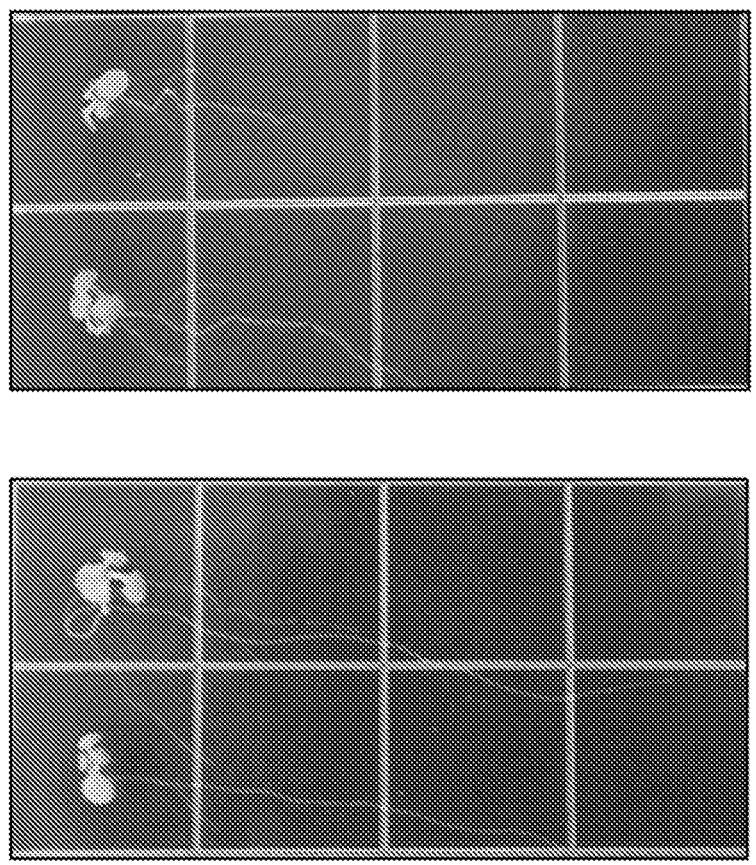
FIG. 2 shows (left panel) normal root development of *Arabidopsis thaliana* when grown in plant nutrient media plus sucrose (PNS). The right panel shows the change in root morphology leading to a shorter primary root and new lateral roots when $C_{14}$ benzyl hydraphile is added at a concentration of 20 μM to PNS media.

FIG. 2 illustrates root development in the presence of PNS and PNS+$C_{14}$. The number of lateral roots observed for 20 µM $C_{14}$ benzyl hydraphile (2) was 6.2±0.3, whereas the lateral root density observed was 0.48±0.08. This is a 4-fold increase in lateral root density caused by the presence of compound 2.

Figure 3:
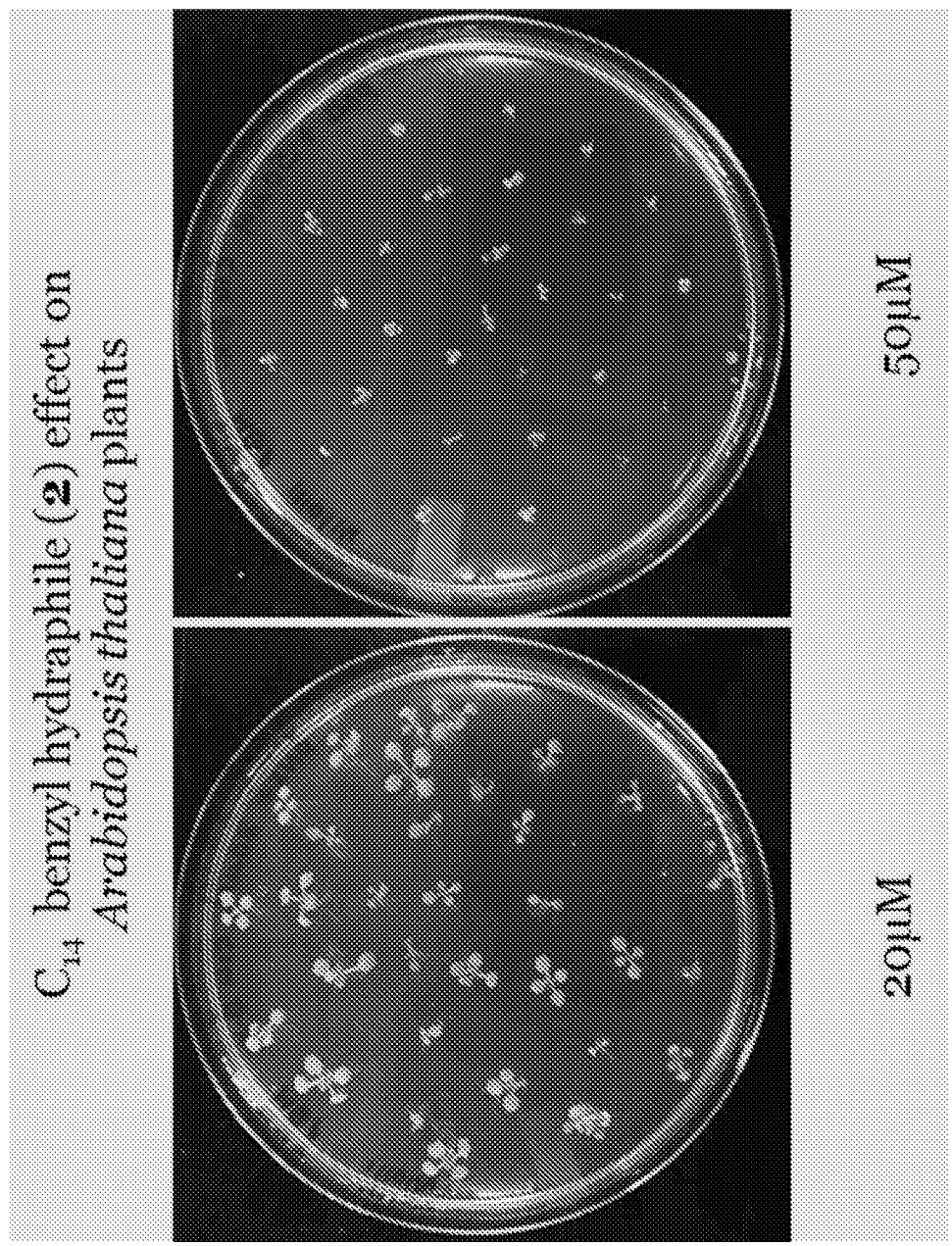
FIG. 3 shows the growth of *Arabidopsis thaliana* in the presence of $C_{14}$ benzyl hydraphile, added to the growth media at concentrations of 20 μM (left) and 50 μM. Growth appears normal at 20 μM but stunted at 50 μM.

FIG. 3 illustrates root development in the presence of $C_{14}$ at different concentrations. At 50 µM C14 benzyl hydraphile, there is a decrease in the primary root length by 98% and an inhibition of lateral root development causing chlorosis of the leaves. This indicates the inhibition of growth and development of plants, which can be due to the toxicity of the hydraphile at this concentration.

Figure 4:
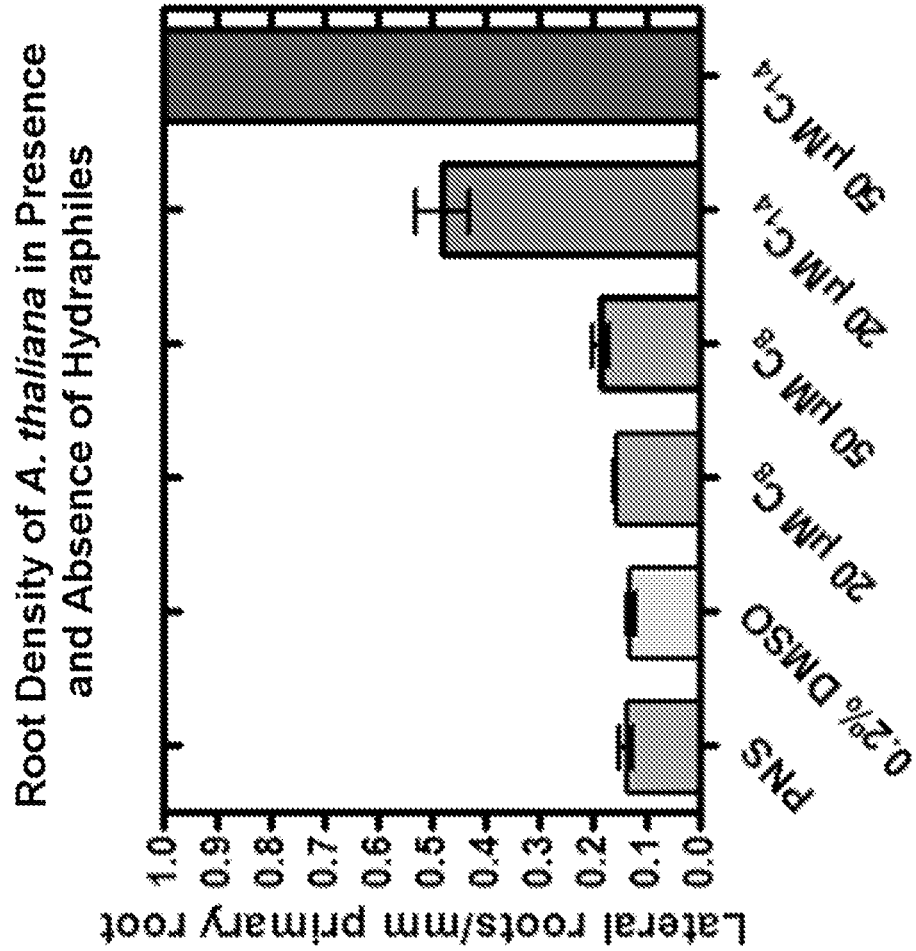
FIG. 4 is a graphical comparison of *Arabidopsis thaliana* germination in the presence of growth media to which various substances have been added.

FIG. 4 is a graphical comparison of the root development in the presence of different growth media showing that the lateral root densities observed with $C_8$ benzyl hydraphile (1) at 20 µM and 50 µM, were 0.15±0.01 and 0.18±0.03, respectively. Within experimental error, $C_8$ benzyl hydraphile did not affect lateral root density.

Without being bound by theory, it is thought that the $C_8$ benzyl hydraphile (1) is not an efficient pore-former, although it can function as an ion transporter. It did not conduct sodium cation efficiently in a study of hydraphiles having various chain lengths ("n" in FIG. 1) as described in the Weber, M. E., Schlesinger, P. H., Gokel, G. W.; Dynamic Assessment of Bilayer Thickness by Varying Phospholipid and Hydraphile Synthetic Channel Chain Lengths. *Journal of the American Chemical Society* 2005, 127(2), 636-642. In this case, the $C_8$ benzyl hydraphile was used as a control. A possible mechanism for the action of hydraphiles is that they affect ion transport and/or compete with endogenous pore-formers. Without being bound by theory, if $C_8$ benzyl hydraphile was inactive and significant changes in root morphology were observed with $C_{14}$ benzyl hydraphile (2), it would correlate to the known ion transport or pore-formation abilities of these two compounds.

In the presence of 20 µM and 50 µM concentrations of $C_8$ benzyl hydraphile (compound 1), the average primary root length was 34±7 mm and 31±6 mm, respectively as recorded in Table 1. The change in primary root length observed with $C_8$ benzyl hydraphile (1) was within experimental error of PNS alone (38 mm) and PNS+DMSO (35 mm) controls. Within experimental error, $C_8$ benzyl hydraphile did not affect the development of primary roots.

As the pore forming and ion transport abilities of benzyl hydraphiles depend significantly on the spacer chain lengths that define the molecule's overall length, the failure of $C_8$ benzyl hydraphile to alter root architecture, is consistent with a mechanism that involves ion transport, although the plant growth could be indifferent to 1 for a variety of reasons. The comparison of the effect of $C_8$ and $C_{14}$ hydraphiles is useful because the two compounds have identical component structures and differ chemically mainly in length and molecular weight.

The difference in the effect on root architecture of $C_8$ benzyl hydraphile (1), which does not form ion channels, and $C_{14}$ benzyl hydraphile (2), which is an excellent ion transporter, is consistent with the channel function of these synthetic amphiphiles. The effect of the ion-transporting hydraphiles in this case is similar to that of the auxins, which affect channel function and both the growth and development of the plant.

Lariat Ethers and Lariat Ether Amides.

Lariat ethers are synthetic amphiphiles that are known to insert in bilayer membranes and transport cations. Recently, it was found that lariat ethers enhance the efficacy of antibiotic function against bacteria when co-administered with appropriate pharmaceuticals.

Certain aspects are drawn to treating a plant by the addition of any one of the lariat ethers or lariat ether amides disclosed herein to a plant. In certain embodiments, a plant is supplemented with a composition comprising the lariat ether or lariat ether amide. In certain embodiments, a plant is contacted with a composition comprising the lariat ether or lariat ether amide. In certain embodiments, the composition comprising the lariat ethers or lariat ether amides is water and/or an aqueous solution. In certain embodiments, the composition comprising the lariat ether or lariat ether amide is either a solid plant growth medium. An illustrative example is a plant nutrient media containing 0.5% sucrose and 0.6% agar. In certain embodiments, the lariat ethers or lariat ether amides is dissolved, suffused, etc., as appropriate for the composition within which it is contained, which can be readily determined by one of ordinary skill in the art. In certain embodiments, the addition of a lariat ether or lariat ether amide to a plant causes a change in plant root morphology such as a change in primary root length and/or a change in lateral root density. In certain embodiments, the addition of a lariat ether or lariat ether amide causes a decrease in primary root length and/or an increase in lateral root density. In certain embodiments, addition inhibits growth of the plant.

Certain illustrative embodiments are shown in Table 2. Lariat ethers and lariat ether amides were added to plant nutrient plus sucrose broth to determine the effect on growth or root morphology. Table 2 shows the results of those studies.

TABLE 2

Effect of lariat ethers or lariat ether amides on the growth of *A. thaliana* when added to PNS growth media.

| | Conc. µM | Primary root length | Percent decrease 1° root | Number lateral roots | Lateral root density |
|---|---|---|---|---|---|
| PNS | n/a | 40.6 | n/a | 6.5 | 0.16 |
| DMSO | 0.2%[a] | 37.9 | 6.7 | 6.3 | 0.17 |
| Lariat ethers[b] | | | | | |
| $C_6$ | 20 | 38.3 | 5.9 | 6.6 | 0.18 |
| $C_6$ | 50 | 33.0 | 18.8 | 4.6 | 0.14 |
| $C_8$ | 20 | 6.8 | 83.4 | 5.1 | 0.64 |
| $C_8$ | 50 | 1.6 | 96.1 | 2.2 | 1.38 |
| $C_{10}$ | 20 | 3.5 | 91.4 | 4 | 1.14 |
| $C_{10}$ | 50 | 2 | 95.1 | 3.5 | 1.75 |
| $C_{12}$ | 20 | 40.1 | 1.3 | 6 | 0.17 |
| $C_{12}$ | 50 | 35.9 | 11.5 | 4.9 | 0.15 |
| $C_{14}$ | 20 | 41.5 | 0 | 6.9 | 0.17 |
| $C_{14}$ | 50 | 20.9 | 48.4 | 4.9 | 0.21 |
| Lariat ether amides[b] | | | | | |
| $C_6$ | 50 | 38.6 | 4.9 | 5.6 | 0.15 |
| $C_7$ | 20 | 22.9 | 45.3 | 4.5 | 0.21 |
| $C_7$ | 50 | 7.3 | 82.5 | 4.2 | 0.65 |
| $C_8$ | 50 | 31.2 | 23.2 | 5.2 | 0.17 |
| $C_9$ | 20 | 9.2 | 78.2 | 1.6 | 0.19 |
| $C_9$ | 50 | 15.7 | 62.6 | 2 | 0.13 |
| $C_{10}$ | 50 | 3.1 | 92.4 | 0.6 | 0.19 |
| $C_{12}$ | 50 | 39.9 | 1.73 | 7 | 0.18 |

TABLE 2-continued

Effect of lariat ethers or lariat ether amides on the growth of *A. thaliana* when added to PNS growth media.

|  | Conc. µM | Primary root length | Percent decrease 1° root | Number lateral roots | Lateral root density |
|---|---|---|---|---|---|
| $C_{13}$ | 20 | 36.9 | 11.8 | 5.1 | 0.14 |
| $C_{13}$ | 50 | 35.6 | 14.9 | 4.2 | 0.14 |
| $C_{14}$ | 50 | 41.9 | 0 | 8.6 | 0.21 |

[a]0.2% by volume.
[b]Total number of carbon atoms in each side arm.

In the series of lariat ethers and lariat ether amides shown, only the $C_8$ and $C_{10}$ lariat ethers shows a significant change in root morphology when administered at 20 µM. Some variation is observed when the concentration of additive is 50 µM, but this concentration borders on being toxic to the plant.

Figure 7:
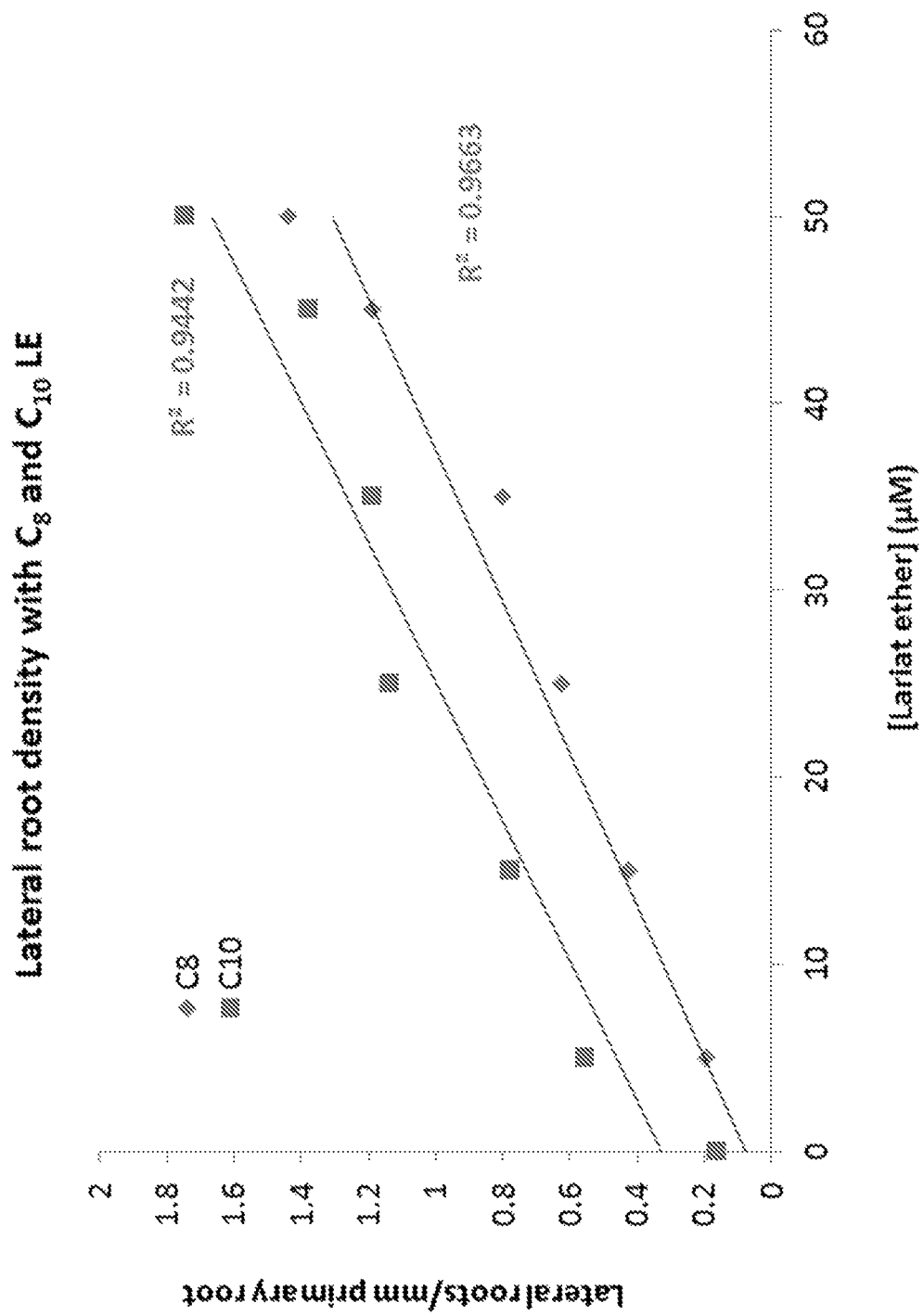
FIG. 7 is a graphical representation of *A. thaliana* lateral root density with increasing concentrations (0 μM to 50 μM) of $C_8$ and $C_{10}$ lariat ether. Linear increase in lateral root density is observed with increasing concentration of $C_8$ and $C_{10}$ lariat ethers.

FIG. 7 shows the relationship between lateral root density and lariat ether concentration. The two compounds studied were 4,13-diaza-18-crown-6 derivatives ($C_8$ and $C_{10}$ lariat ethers) having linear $C_8$ or $C_{10}$ alkyl side arms. The two compounds were administered to the growth medium in concentrations of 5, 15, 25, 35, 45, and 50 µM. For both compounds, the calculated value for lateral roots divided by length (in mm) of the primary root was graphed on the ordinate as a function of concentration. The two data sets were modeled by linear regression which shows a straight line relationship in both cases. The "goodness of fit" or correlation parameter ($R^2$) was 0.97 for $C_8$ and 0.94 for $C_{10}$.

Synthetic Anion Transporters.

Synthetic anion transporters ("SATs") that are present in this disclosure are amphiphiles that facilitate the transport of anions across bilayer membranes. These compounds contain four structural modules. They are (1) hydrophobic anchor chains, (2) a linker element that is typically a diacid, (3) a peptide, and (4) a C-terminal residue appended to the carboxyl group.

Figure 11:
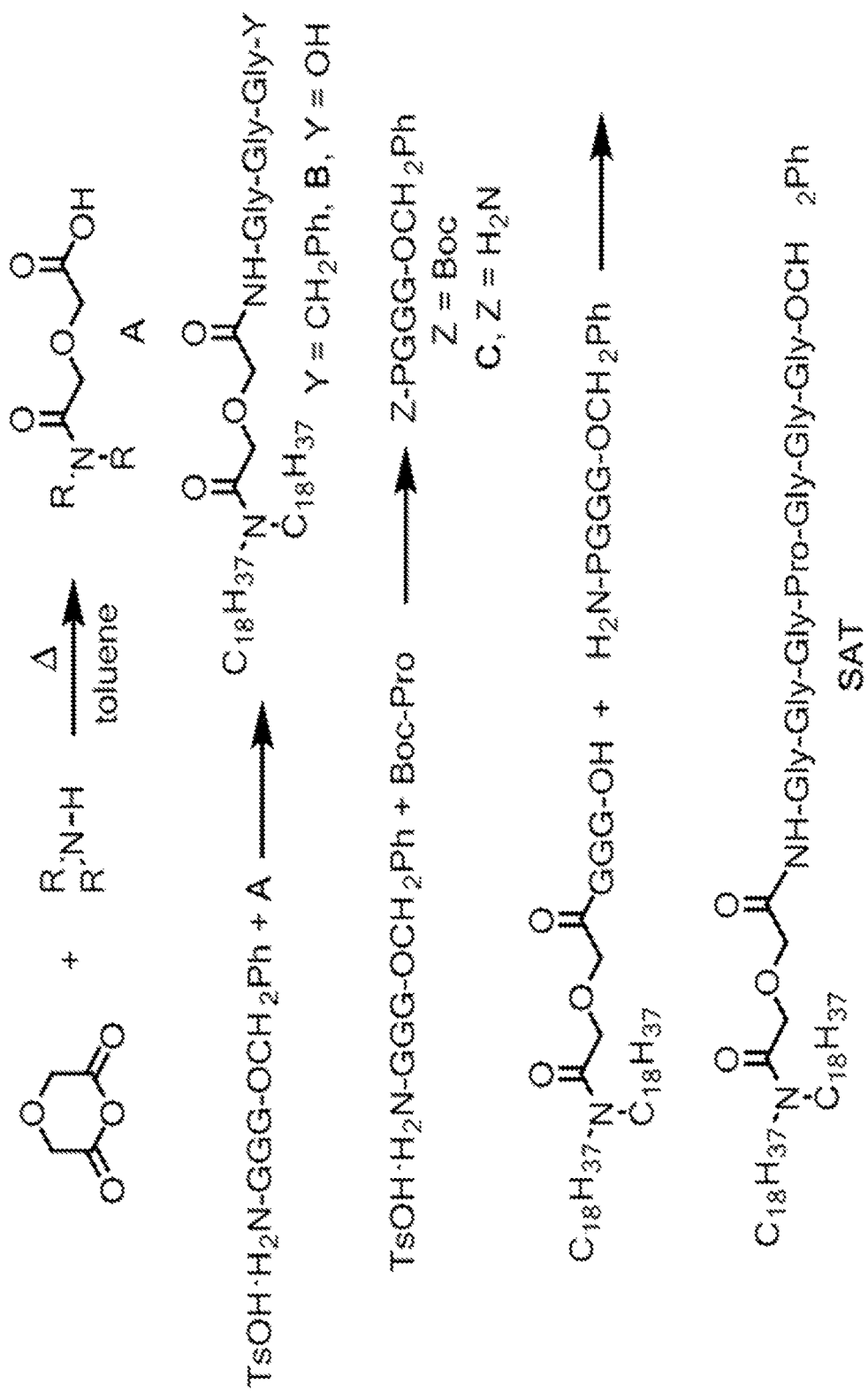
FIG. 11 shows a representative synthetic scheme for the preparation of $(C_{18}H_{37})_2NCOCH_2OCH_2CO$-GGGPGGG-$OC_7H_{15}$ synthetic anion transporter (SAT).

Table 3 illustrates chemical structures of the synthetic anion transporter ("SAT") synthetic amphiphiles. Table 3 shows several representative compounds. Further, a representative synthetic scheme for the SAT compounds is shown in FIG. 11.

TABLE 3

Structures of Compounds 4-24[a]

| No. | Twin anchors | Linker | Peptide |
|---|---|---|---|
| 4 | n-$C_6H_{13}$ | ~$COCH_2CH_2CO$~ | GGGPGGG |
| 5 | n-$C_{10}H_{21}$ | ~$COCH_2CH_2CO$~ | GGGPGGG |
| 6 | n-$C_{12}H_{25}$ | ~$COCH_2CH_2CO$~ | GGGPGGG |
| 7 | n-$C_{18}H_{37}$ | ~$COCH_2CH_2CO$~ | GGGPGGG |
| 8 | n-$C_6H_{13}$ | ~$COCH_2OCH_2CO$~ | GGGPGGG |
| 9 | n-$C_{18}H_{37}$ | ~$COCH_2OCH_2CO$~ | GGGPGGG |
| 10 | n-$C_{12}H_{25}$ | ~$COCH_2CH_2CO$~ | AAAPGGG |
| 11 | n-$C_{18}H_{37}$ | ~$COCH_2CH_2CO$~ | AAAPGGG |
| 12 | n-$C_{12}H_{25}$ | ~$COCH_2OCH_2CO$~ | AAAPGGG |
| 13 | n-$C_{18}H_{37}$ | ~$COCH_2OCH_2CO$~ | AAAPGGG |
| 14 | n-$C_{18}H_{37}$ | ~$COCH_2SCH_2CO$~ | AAAPGGG |
| 15 | n-$C_{12}H_{25}$ | ~$COCH_2CH_2CO$~ | GGGPSGS |
| 16 | n-$C_{18}H_{37}$ | ~$COCH_2CH_2CO$~ | GGGPSGS |
| 17 | n-$C_{18}H_{37}$ | ~$COCH_2OCH_2CO$~ | GGGPSGS |
| 18 | n-$C_{12}H_{25}$ | ~$COCH_2CH_2CO$~ | GGGPS(t-Bu)GS(t-Bu) |
| 19 | n-$C_{18}H_{37}$ | ~$COCH_2CH_2CO$~ | GGGPS(t-Bu)GS(t-Bu) |
| 20 | n-$C_{12}H_{25}$ | ~$COCH_2OCH_2CO$~ | GGGPS(t-Bu)GS(t-Bu) |
| 21 | n-$C_{18}H_{37}$ | ~$COCH_2OCH_2CO$~ | GGGPS(t-Bu)GS(t-Bu) |
| 22 | n-$C_{12}H_{25}$ | ~$COCH_2CH_2CO$~ | GGGPGS(t-Bu)G |
| 23 | n-$C_{18}H_{37}$ | ~$COCH_2CH_2CO$~ | GGGPGS(t-Bu)G |
| 24 | n-$C_{18}H_{37}$ | ~$COCH_2OCH_2CO$~ | GGGPGS(t-Bu)G |

Figure 8:
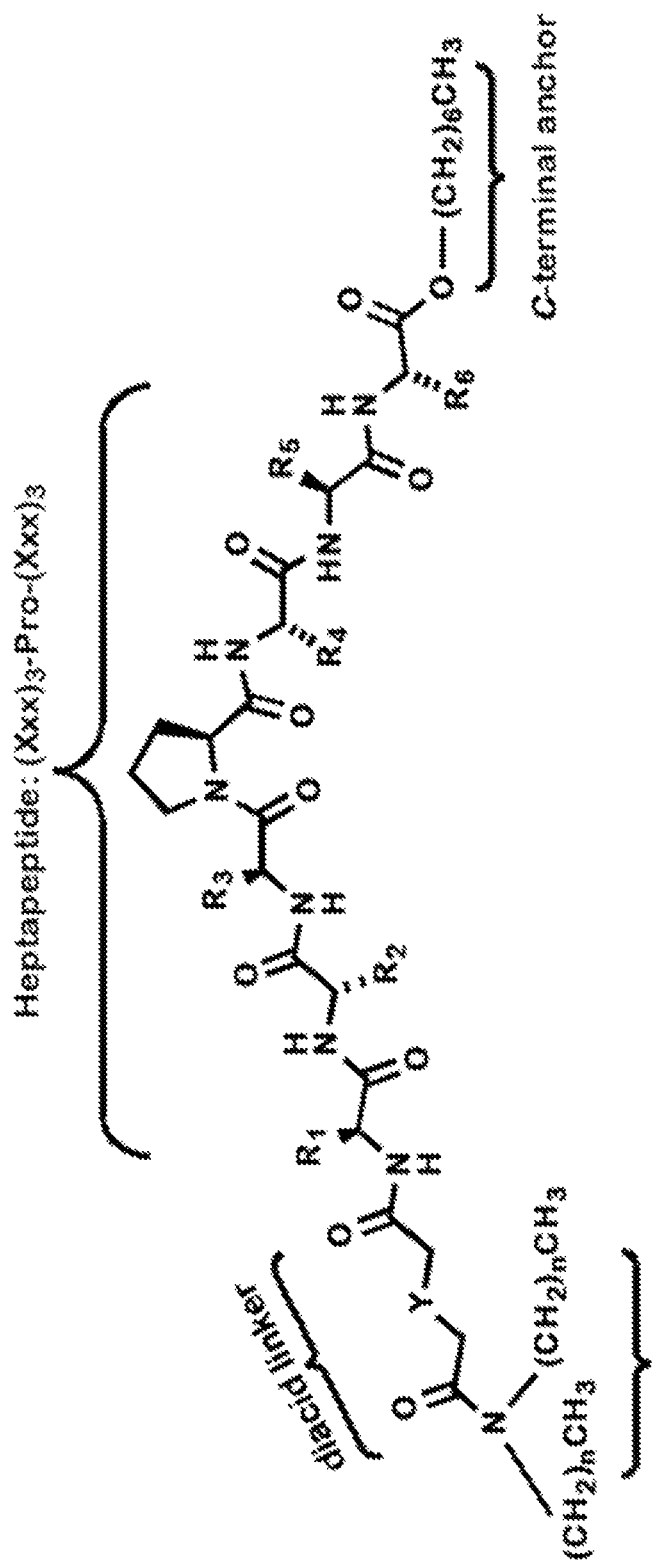
FIG. 8 illustrates the chemical structure of representative synthetic anion transporters (SATs).
Figure 9:
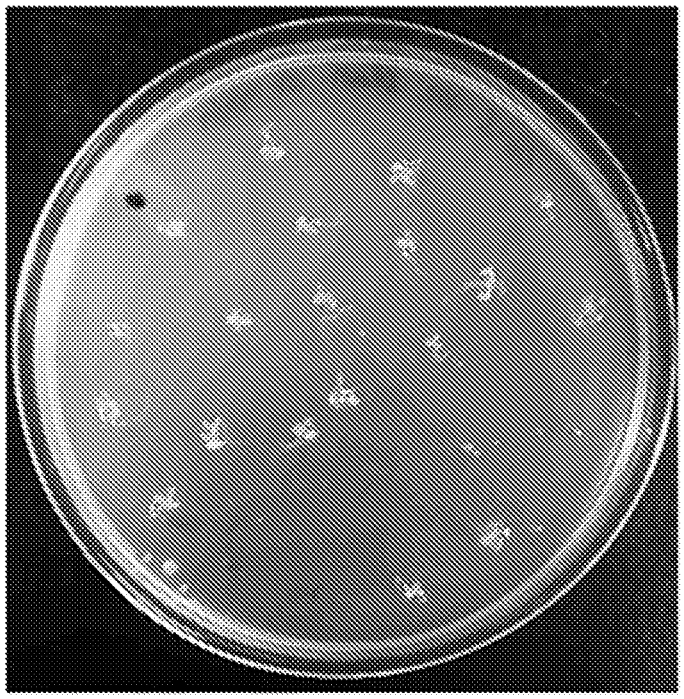
FIG. 9 shows (left panel) normal root development of *Arabidopsis thaliana* when grown in plant nutrient media plus sucrose (PNS). The right panel shows the change in root morphology leading to a shorter primary root and new lateral roots when $(C_{12}H_{25})_2NCOCH_2CH_2CO$-GGGPSGS-$OC_7H_{15}$ is added at a concentration of 50 μM to PNS media.
Figure 9:
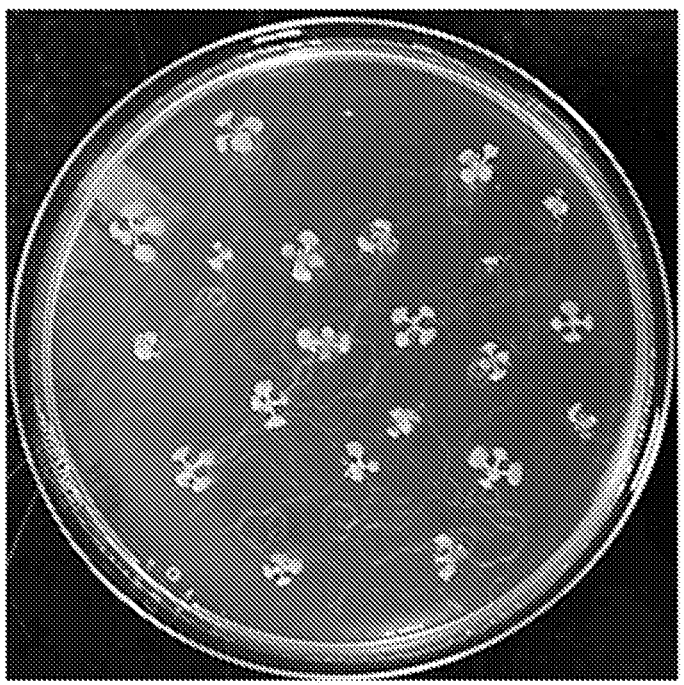

[a]All compounds have a C-terminal n-heptyl anchor (see FIG. 8).

Certain aspects are drawn to treating a plant by the addition of any one of the SATs disclosed herein to a plant. In certain embodiments, a plant is supplemented with a composition comprising the SAT. In certain embodiments, a plant is contacted with a composition comprising the SAT. In certain embodiments, the composition comprising the SAT is water and/or an aqueous solution. In certain embodiments, the composition comprising the SAT is a solid plant growth medium. An illustrative example is a plant nutrient media containing 0.5% sucrose and 0.6% agar. In certain embodiments, the SAT is dissolved, suffused, etc., as appropriate for the composition within which it is contained, which can be readily determined by one of ordinary skill in the art. In certain embodiments, the addition of an SAT to a plant causes a change in plant root morphology such as a change in primary root length and/or a change in lateral root density. In certain embodiments, the addition of an SAT causes a decrease in primary root length and/or an increase in lateral root density. In certain embodiments, addition inhibits growth of the plant.

Illustrative of certain embodiments, approximately 60 plants were grown on PNS media (no additives) and root lengths and the number of lateral roots were recorded for each. The data points were averaged to obtain the following baseline values: primary root length=40.4±3.8 mm and number of lateral roots=6.1±0.8, respectively. The lateral root density was obtained by dividing the number of lateral roots by the length (in mm) of the primary root. The control value was (6.1/40.6=) 0.15.

Test compounds were added to the growth medium as 0.2% by volume DMSO. A control for DMSO (60 plants) showed no effect was observed on growth or on root morphology compared to the PNS control absent DMSO (data not shown). Each SAT was added to a concentration of 50 µM in the PNS/agar growth medium.

2,4-Dichlorophenoxyacetic acid (2,4-D) is a well-known, broad leaf herbicide was used as a positive control. 2,4-D was present in the PNS medium at a concentration of 100 nM and plants were grown as noted above. 2,4-D significantly decreases both primary root length and lateral root density to 3.9±0.6 and 3.4±0.6, respectively. The calculated lateral root density in this case was 0.85.

Table 4 shows the results of exposing *Arabidopsis thaliana* to SAT compounds 4-24. Each compound was suffused into plant growth medium (PNS) at a concentration of 50 µM.

TABLE 4

| Compound Number (50 µM) | Primary root length (mm) | Number of lateral roots | Lateral root density |
|---|---|---|---|
| PNS (±0.2% DMSO) | 40.4 ± 3.8 | 6.1 ± 0.8 | 0.15 ± 0.01 |
| 2,4-D (100 nM) | 3.9 ± 0.6 | 3.4 ± 0.6 | 0.85 ± 0.12 |
| GGGPGGG | | | |
| Compound 4 | 30.9 ± 0.3 | 4.7 ± 0.2 | 0.16 ± 0.01 |
| Compound 5 | 29.4 ± 4.6 | 3.9 ± 0.7 | 0.14 ± 0.01 |
| Compound 6 | 30.5 ± 0.6 | 4.4 ± 0.8 | 0.15 ± 0.03 |

TABLE 4-continued

| Compound Number (50 μM) | Primary root length (mm) | Number of lateral roots | Lateral root density |
|---|---|---|---|
| Compound 7 | 30.6 ± 4.3 | 3.9 ± 0.7 | 0.13 ± 0.01 |
| Compound 8 | 28.4 ± 5.4 | 6.6 ± 2.2 | 0.23 |
| Compound 9 | 40.5 ± 3.4 | 6.8 ± 1.3 | 0.17 ± 0.02 |
| AAAPGGG | | | |
| Compound 10 | 28.4 | 3.4 | 0.12 |
| Compound 11 | 39.4 ± 6.5 | 6.1 ± 1.2 | 0.16 ± 0.01 |
| Compound 12 | 43.2 ± 8.0 | 6.5 ± 0.9 | 0.15 ± 0.01 |
| Compound 13 | 36.9 ± 10.5 | 5.2 ± 2.0 | 0.14 ± 0.02 |
| Compound 14 | 40.3 ± 10.1 | 7.0 ± 1.7 | 0.17 |
| GGGPSGS | | | |
| Compound 15 | 9.0 ± 1.2 | 4.5 ± 0.4 | 0.51 ± 0.03 |
| Compound 16 | 46.0 ± 12.0 | 8.7 ± 4.9 | 0.17 ± 0.06 |
| Compound 17 | 40.9 ± 10.8 | 6.2 ± 2.4 | 0.15 ± 0.02 |
| GGGPS(t-Bu)GS(t-Bu) | | | |
| Compound 18 | 30.2 ± 7.3 | 5.8 ± 0.7 | 0.20 ± 0.03 |
| Compound 19 | 28.3 | 5.9 | 0.15 |
| Compound 20 | 35.5 ± 2.5 | 5.9 ± 0.2 | 0.17 ± 0.02 |
| Compound 21 | 29.3 ± 5.9 | 5.2 ± 0.3 | 0.21 ± 0.05 |
| GGGPGS(t-Bu)G | | | |
| Compound 22 | 47.3 ± 0.5 | 7.9 ± 0.5 | 0.17 ± 0.01 |
| Compound 23 | 48.2 ± 0.7 | 8.2 | 0.17 |
| Compound 24 | 47.7 ± 1.7 | 6.8 | 0.15 ± 0.01 |

The most extensively studied SAT compounds have a GGGPGGG (Gly-Gly-Gly-Pro-Gly-Gly-Gly) heptapeptide sequences. These compounds were designed to be chloride ion transporters. Planar bilayer conductance data confirmed this capability and function. Compounds 4-10 have the GGGPGGG peptide sequence, but differ both in the anchor and linker chains. The primary root length and number of lateral roots for 9 is within experimental error of the PNS control. The average primary root length for 4-8 is 30 mm, which compares with 40.4 mm for the PNS control.

The linkers in 4-7 are succinic acid (Y of Formula IV is absent) and diglycolic acid (Y=O) in 8 and 9. Direct comparisons can be made between compounds 4 and 8, which have n-hexyl N-terminal anchors and 7 and 9 which have n-octadecyl twin tails respectively. Thus, the structural differences in these compound pairs reside in the linkers (O present vs. O absent). Table 4 shows that 9 is essentially identical control but 7 shows diminished primary root length and lateral root number. Since both variables are reduced in 7 compared to 9, no net effect is observed on lateral root density. Compounds 4-8 caused diminished growth rate.

The heptapeptide sequence in compounds 10-14 is AAAPGGG (Ala-Ala-Ala-Pro-Gly-Gly-Gly). Compounds 10 and 11 have succinyl linkers (Y is absent in Figure IV) and 12 and 13 are linked by diglycolic acid diamide. A different linker is present in 11, which has the structure $(C_{18})_2NCOCH_2SCH_2CO$-AAAPGGG-$OC_7$. The linker here is thiodiglycolic acid (Formula IV, Y=S). In short, no significant deviation from control was observed with 11-14 despite variations in linker and anchor chain length. Compound 9 can be compared directly to 13. Their structures are identical except for the GGGPGGG (9) vs. AAAPGGG (13) peptide sequences. Neither compound differs from the control in its biological effect on *A. thaliana*.

Compound 10, however, which has the structure $(C_{12})_2NCOCH_2CH_2CO$-AAAPGGG-$OC_7$, showed primary root length comparable to that observed for 4-8, but an even smaller number of lateral roots. SATs 10 and 11 are identical except for the N-terminal anchor chains, which are n-dodecyl in 10 and n-octadecyl in 11. In an earlier study, it was shown that $Cl^-$ transport was greater for $(C)_2NCOCH_2OCH_2CO$-GGGPGGG-$OCH_2Ph$ when $C_n$ was n-dodecyl compared to n-octadecyl. It was concluded that the latter compound was more selective but less efficient and that the former likely was transporting both $Na^+$ and $Cl^-$ ions. Without being bound by theory, if a similar effect on ion transport occurs in the case of 10, it could explain the difference between the activity of 10 and 11. This is not expected to be the only effect as the anchor chain difference is present in 12 and 13, which are otherwise comparable, and they are similar to controls.

It is also noted that that 13 and 14 behave in a fashion similar to each other and to controls despite the difference in linkers. The two compounds are identical except for the presence of sulfur (14) compared to oxygen (13) in the linker chains.

Certain of the compounds disclosed herein are SATs containing one or more serine residues in the heptapeptide sequence. Ten compounds were prepared that incorporate one or more serines into the heptapeptide sequence. Table 4 shows the compounds in three groups. The peptides were prepared by coupling a GGGP fragment to either an SGS or GSG segment in which the serine hydroxyl groups were protected as the t-butyl ethers. As a result, the 15-17 with free hydroxyl groups and 18-24 in their protected forms were obtained.

The simplest compounds in the group 18-24 are 22-24, in which the single serine in the GGGPGSG sequence is protected by t-butyl. Compounds 23 and 24 differ in having succinyl and diglycoyl linkers but are otherwise identical. Compound 22 has the succinyl linker chain of 23 but has twin dodecyl anchor chains rather than the octadecyl chains present in both 23 and 24. The average primary root length measured for 22-24 was 47.7 mm and the variation in this value was small. It is significantly longer (~20%) than the control value of 40.4 mm. Likewise, the average number of lateral roots (7.6) is about 25% greater than control. Since the lateral root density is higher and the primary root length is longer, the lateral root density is similar to the control value. Overall, it appears that this group of SATs stimulates growth without altering growth characteristics.

The results observed for the bis(serinyl) di-t-buyl ethers in 18-21 approximately parallel those observed for 4-8 and seem to be the opposite of the effect observed for 22-24.

Figure 10:
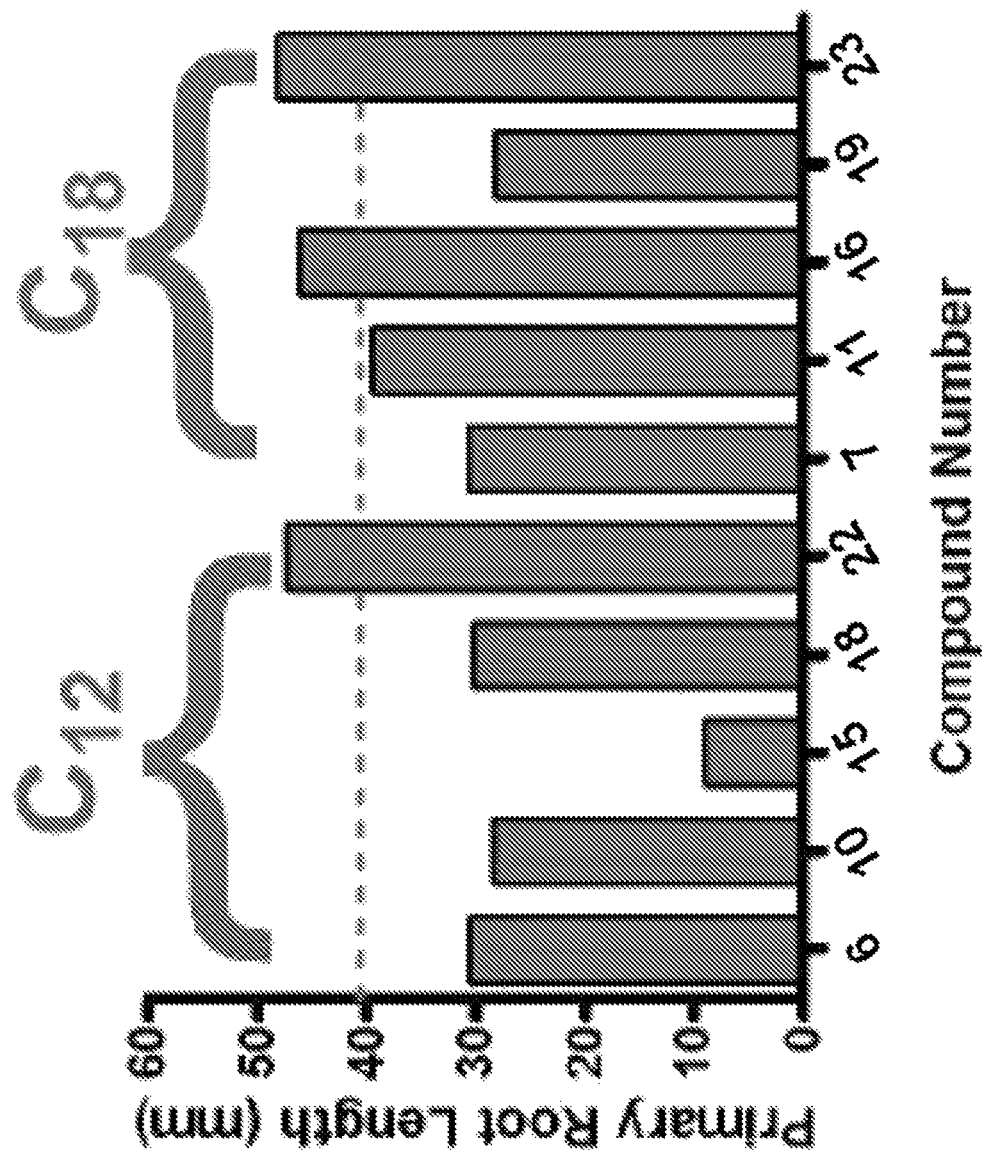
FIG. 10 shows a comparison of primary root lengths in pairs of compounds having $C_{12}$ and $C_{18}$ N-terminal anchors and succinyl linkers. The pairs have the following heptapeptide sequences: 6,7 (GGGPGGG); 10,11 (AAAPGGG); 15,16 (GGGPSGS); 19,20; [GGGPS(t-Bu)GS(t-Bu)]; and 22,23 [GGGPGS(t-Bu)G]. The dashed line indicates the primary root length of the controls.

FIG. 10 shows a comparison of heptapeptide sequence effects. Two sets of compounds have identical N- and C-terminal anchor chains and succinyl linkers. They are 6,7; 10,11; 15,16; 18,19; and 22,23. These pairs have $C_{12}$ and $C_{18}$ N-terminal anchor chains, respectively, but otherwise are identical. The pairs differ from one another in the heptapeptide sequences. FIG. 10 shows the effect of peptide sequence on primary root length. Plants grown under control conditions have a primary root length of 40.4 mm, as indicated in the graph by the dashed line. The pairs have the following heptapeptide sequences: 6,7 (GGGPGGG); 10,11 (AAAPGGG); 15,16 (GGGPSGS); 18,19; [GGGPS(t-Bu)GS(t-Bu)]; and 22,23 [GGGPGS(t-Bu)G]. The dashed line indicates the primary root length of the controls.

Two compounds show primary root lengths significantly greater than controls. They are 22 and 23 [$C_{12}$ and $C_{18}$ GGGPGS(t-Bu)G]. Both compounds contain serine and all three stimulate primary root length to about the same extent (see Table 4). The $C_{18}$ SAT having the AAAPGGG peptide (11) shows no effect on primary root length. Compounds 6, 7, 10, 18, and 19 all affect *A. thaliana* growth by diminishing primary root length. That the 6,7 and 18,19 pairs behave the same suggests that it is the peptide sequence that is important rather than the N-terminal chain length. However, compound 10 reduces primary root length while its partner, 8, shows no effect, suggesting that the peptide sequence itself cannot account for the difference.

The most striking results were observed with the 15,16 pair. In both cases, the heptapeptide sequence is GGGPSGS. The N-terminal anchor chains are $C_{12}$ in 15 and $C_{18}$ in 16. The former shows a dramatic reduction in primary root length and the latter an increase outside of experimental error relative to control. In a previous study, it was found that the amide hydrogens of amino acids $^5$G and $^7$G were the key Cl$^-$-binding donors when studied by NMR in a micellar matrix. (Cook, G. A.; Pajewski, R.; Aburi, M.; Smith, P. E.; Prakash, O.; Tomich, J. M.; Gokel, G. W., NMR structure and dynamic studies of an anion-binding, channel-forming heptapeptide, *J. Am. Chem. Soc.* 2006, 128, 1633-8). At present, there is no direct evidence that Cl$^-$—or any ion—binding is critical to the effect these compounds have on plants. Notwithstanding, the difference in effect on *A. thaliana* by 15 and 16 is dramatic and striking.

Figure 12:
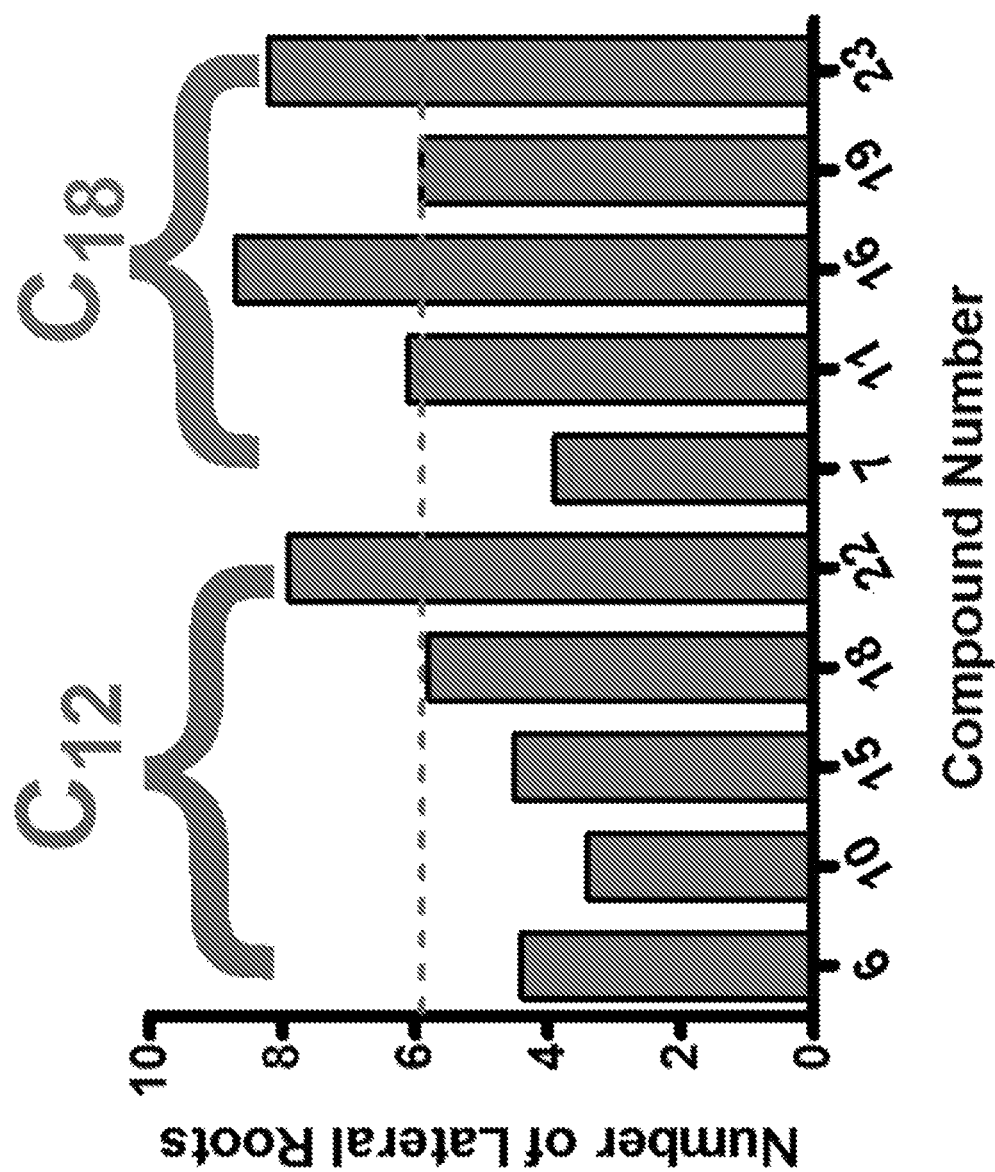
FIG. 12 is a comparison of the number of lateral roots observed in pairs of compounds having $C_{12}$ and $C_{18}$ N-terminal anchors and succinyl linkers. The pairs have the following heptapeptide sequences: 6,7 (GGGPGGG); 10,11 (AAAPGGG); 15,16 (GGGPSGS); 19,20; [GGGPS(t-Bu)GS(t-Bu)]; and 22,23 [GGGPGS(t-Bu)G]. The dashed line indicates the lateral root number of the controls.
Figure 13:
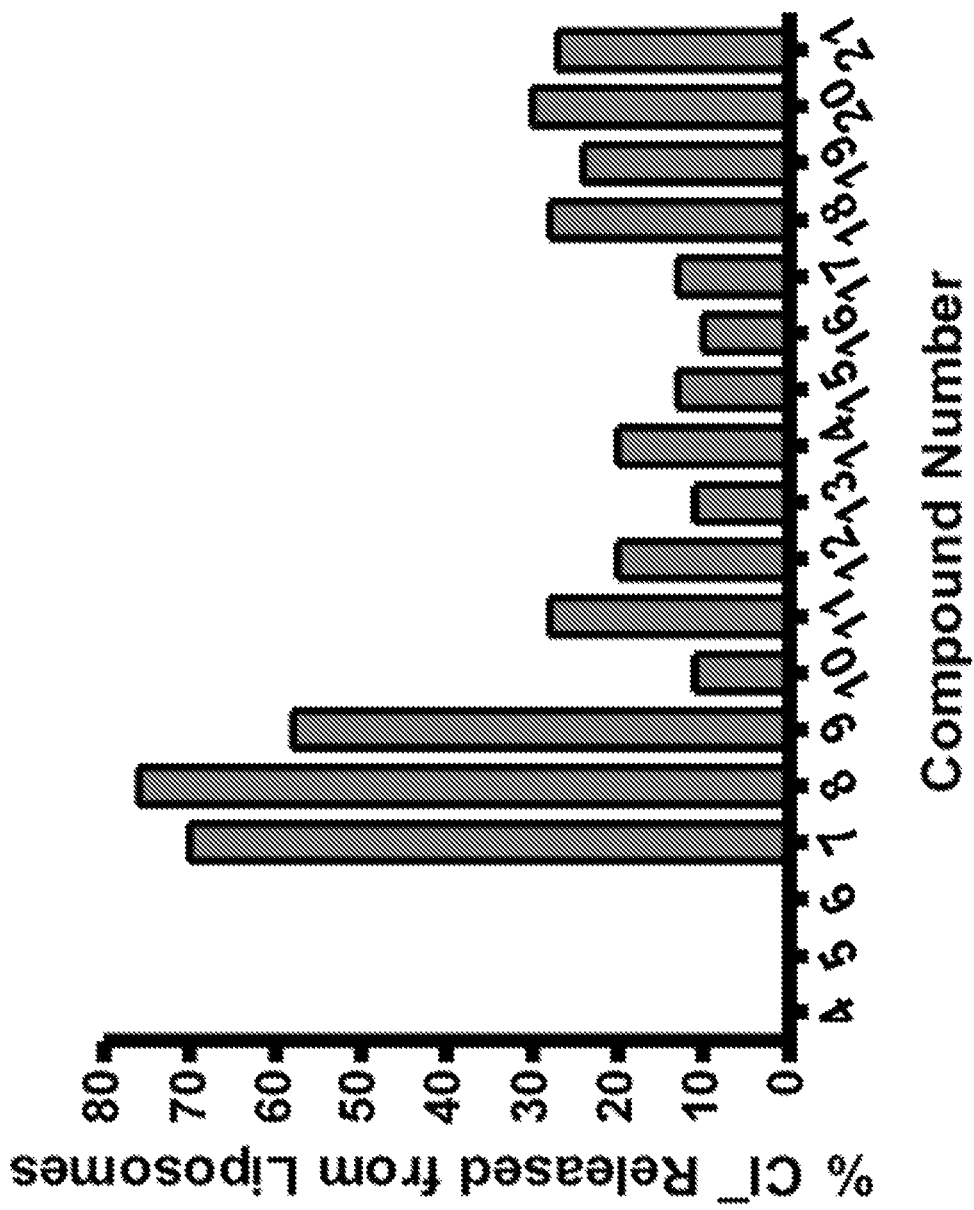
FIG. 13 shows a graphical representation of ion release from liposomes.

The results shown in FIG. 12 parallel those of FIG. 10, i.e., they show the effect of the same compounds on the number of lateral roots observed when administered to *A. thaliana*. As with primary root length, compounds 16, 22, and 24 show enhancements relative to controls. As with primary root length, 11 shows no effect on lateral root number. In contrast, compounds 6, 7, 18, and 19 showed similar, reduced primary root length, but the number of lateral roots is unaltered by the presence of 18 and 19. The lateral root number is diminished by the presence of 7 and 10 by an approximately equal amount and 15 does not show such a dramatic effect as is apparent in primary root length. FIG. 12 shows a comparison of the number of lateral roots observed in pairs of compounds having $C_{12}$ and $C_{18}$ N-terminal anchors and succinyl linkers. The pairs have the following heptapeptide sequences: 6,7 (GGGPGGG); 10,11 (AAAPGGG); 15,16 (GGGPSGS); 18,19; [GGGPS(t-Bu)GS(t-Bu)]; and 22,23 [GGGPGS(t-Bu)G]. The dashed line indicates the lateral root number of the controls.

Figure 6:
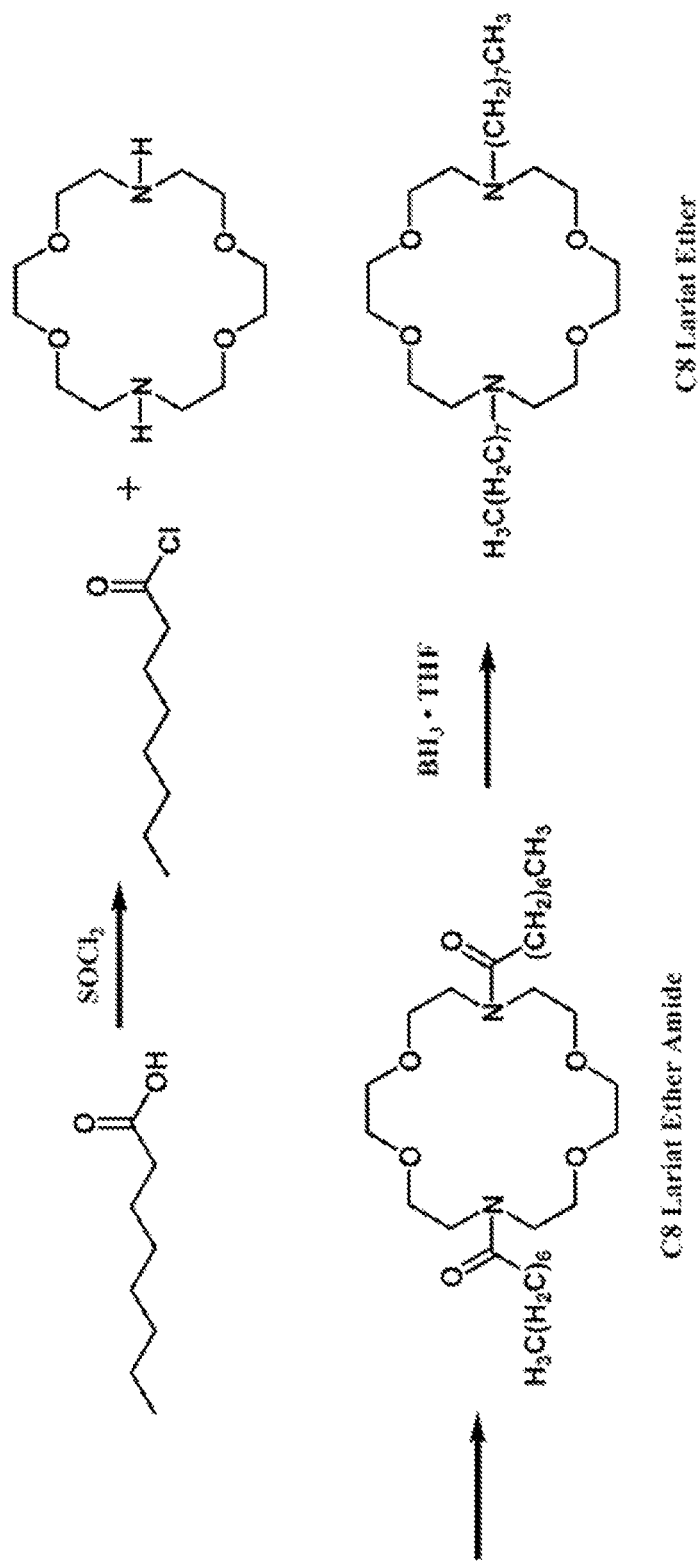
FIG. 6 is a representative synthetic scheme for the preparation of N,N'-di-n-octyl-4,13-diaza-18-crown-6.

A possible explanation for the activity of SAT compounds in *A. thaliana* is that they can alter ionic concentrations in the growing plant. FIG. 6 shows a survey of the ability of various SAT compounds to release ions from synthetic vesicles. It is well known that changes in ion concentrations can affect plant growth and development.

It has been discovered that synthetic amphiphiles are effective in promoting lateral root growth at lower concentrations but diminish the growth of the primary roots. The concentration ranges of the synthetic anion transporters (SATs) for promoting lateral root growth in plants vary depending on the plant species and/or the particular synthetic amphiphiles employed. Furthermore, in another aspect, a composition having a high synthetic amphiphile concentration, such as a high synthetic anion transporter concentration, can be employed as a herbicide for undesired plants, such as by spraying a composition comprising such composite onto the leaves of growing plants.

In certain embodiments, a plant is treated by contacting it with water and/or an aqueous solution comprising a synthetic amphiphile and/or synthetic anion transporter disclosed herein. In certain embodiments, the concentration in water is about 0.001 μM, 0.01 μM, 0.1 μM, 1 μM, 5 μM, 10 μM, 15 μM, 20 μM, 25 μM, 30 μM, 40 μM, 50 μM, 60 μM, 75 μM, or 100 μM. In certain embodiments, the concentration in water is about 0.001 μM to about 1 μM, 5 μM, 10 μM, 15 μM, 20 μM, 25 μM, 30 μM, 40 μM, 50 μM, 60 μM, 75 μM, or 100 μM. In certain embodiments, the concentration in water is about 0.01 μM to about 1 μM, 5 μM, 10 μM, 15 μM, 20 μM, 25 μM, 30 μM, 40 μM, 50 μM, 60 μM, 75 μM, or 100 μM. In certain embodiments, the concentration in water is about 0.1 μM to about 1 μM, 5 μM, 10 μM, 15 μM, 20 μM, 25 μM, 30 μM, 40 μM, 50 μM, 60 μM, 75 μM, or 100 μM. In certain embodiments, the concentration in water is about 1.0 μM to about 1 μM, 5 μM, 10 μM, 15 μM, 20 μM, 25 μM, 30 μM, 40 μM, 50 μM, 60 μM, 75 μM, or 100 μM. In certain embodiments, the concentration in water is about 5.0 μM to about 10 μM, 15 μM, 20 μM, 25 μM, 30 μM, 40 μM, 50 μM, 60 μM, 75 μM, or 100 μM. In certain embodiments, the concentration in water is about 10 μM to about 15 μM, 20 μM, 25 μM, 30 μM, 40 μM, 50 μM, 60 μM, 75 μM, or 100 μM. In certain embodiments, the concentration in water is about 25 μM to about 30 μM, 40 μM, 50 μM, 60 μM, 75 μM, or 100 μM. In certain embodiments, the concentration in water is about 50 μM to about 60 μM, 70 μM, 75 μM, 80 μM, 90 μM or 100 μM.

In certain embodiments, a plant is treated by contacting it with an aqueous media comprising a synthetic amphiphile and/or synthetic anion transporters disclosed herein. In certain embodiments, the concentration in the aqueous media is about 0.001 μM, 0.01 μM, 0.1 μM, 1 μM, 5 μM, 10 μM, 15 μM, 20 μM, 25 μM, 30 μM, 40 μM, 50 μM, 60 μM, 75 μM, or 100 μM. In certain embodiments, the concentration in the aqueous media is about 0.001 μM to about 1 μM, 5 μM, 10 μM, 15 μM, 20 μM, 25 μM, 30 μM, 40 μM, 50 μM, 60 μM, 75 μM, or 100 μM. In certain embodiments, the concentration in the aqueous media is about 0.01 μM to about 1 μM, 5 μM, 10 μM, 15 μM, 20 μM, 25 μM, 30 μM, 40 μM, 50 μM, 60 μM, 75 μM, or 100 μM. In certain embodiments, the concentration in the aqueous media is about 0.1 μM to about 1 μM, 5 μM, 10 μM, 15 μM, 20 μM, 25 μM, 30 μM, 40 μM, 50 μM, 60 μM, 75 μM, or 100 μM. In certain embodiments, the concentration in the aqueous media is about 1.0 μM to about 1 μM, 5 μM, 10 μM, 15 μM, 20 μM, 25 μM, 30 μM, 40 μM, 50 μM, 60 μM, 75 μM, or 100 μM. In certain embodiments, the concentration in the aqueous media is about 5.0 μM to about 10 μM, 15 μM, 20 μM, 25 μM, 30 μM, 40 μM, 50 μM, 60 μM, 75 μM, or 100 μM. In certain embodiments, the concentration in the aqueous media is about 10 μM to about 15 μM, 20 μM, 25 μM, 30 μM, 40 μM, 50 μM, 60 μM, 75 μM, or 100 μM. In certain embodiments, the concentration in the aqueous media is about 25 μM to about 30 μM, 40 μM, 50 μM, 60 μM, 75 μM, or 100 μM. In certain embodiments, the concentration in the aqueous media is about 50 μM to about 60 μM, 70 μM, 75 μM, 80 μM, 90 μM or 100 μM.

In certain embodiments, a plant is treated by contacting it with a solid media comprising a synthetic amphiphile and/or synthetic anion transporters disclosed herein. In certain embodiments, the concentration in the solid media is about 0.001 μM, 0.01 μM, 0.1 μM, 1 μM, 5 μM, 10 μM, 15 μM, 20 μM, 25 μM, 30 μM, 40 μM, 50 μM, 60 μM, 75 μM, or 100 μM. In certain embodiments, the concentration in the solid media is about 0.001 μM to about 1 μM, 5 μM, 10 μM, 15 μM, 20 μM, 25 μM, 30 μM, 40 μM, 50 μM, 60 μM, 75 μM, or 100 μM. In certain embodiments, the concentration in the solid media is about 0.01 μM to about 1 μM, 5 μM, 10 μM, 15 μM, 20 μM, 25 μM, 30 μM, 40 μM, 50 μM, 60 μM, 75 μM, or 100 μM. In certain embodiments, the concentration in the solid media is about 0.1 μM to about 1 μM, 5 μM, 10 μM, 15 μM, 20 μM, 25 μM, 30 μM, 40 μM, 50 μM, 60 μM, 75 μM, or 100 μM. In certain embodiments, the concentration in the solid media is about 1.0 μM to about 1 μM, 5 μM, 10 μM, 15 μM, 20 μM, 25 μM, 30 μM, 40 μM, 50 μM, 60

μM, 75 μM, or 100 μM. In certain embodiments, the concentration in the solid media is about 5.0 μM to about 10 μM, 15 μM, 20 μM, 25 μM, 30 μM, 40 μM, 50 μM, 60 μM, 75 μM, or 100 μM. In certain embodiments, the concentration in the solid media is about 10 μM to about 15 μM, 20 μM, 25 μM, 30 μM, 40 μM, 50 μM, 60 μM, 75 μM, or 100 μM. In certain embodiments, the concentration in the solid media is about 25 μM to about 30 μM, 40 μM, 50 μM, 60 μM, 75 μM, or 100 μM. In certain embodiments, the concentration in the solid media is about 50 μM to about 60 μM, 70 μM, 75 μM, 80 μM, 90 μM or 100 μM.

The concentration range can vary depending on the plant species and/or the particular synthetic hydraphile employed. When n is 14 or 16, hydraphile, $C_{14}$ or $C_{16}$, respectively, achieves high inhibition to primary root development (in other words, increases lateral root density) at concentrations up to about 25 μM. At concentrations of from about 50 μM to about 100 μM of $C_{14}$ or $C_{16}$ hydraphile, the primary root development is inhibited by greater than 90%, which exhibits toxic effects on development and growth of the plant.

The concentration range can vary depending on the plant species and/or the particular synthetic lariat ether employed. When n is 7 or 9, lariat ether, $C_8$ or $C_{10}$, respectively, achieves high inhibition against the primary root development and fosters lateral root growth at the lower end of the concentration range. At concentrations ranging from ~25 μM or higher of $C_6$ to $C_{22}$ lariat ethers, the primary root development is inhibited by greater than 90%, having toxic effects on the development and growth of the plant.

The concentration range can vary depending on the plant species and/or the particular synthetic lariat ether amide employed. At concentrations ranging from ~25 μM or higher of $C_6$ to $C_{22}$ lariat ether amides, the primary root development is inhibited by greater than 90%, having toxic effects on the development and growth of the plant.

The compound defined by Formula IV can be administered at certain concentration ranges. The concentration range can vary depending on the plant species and/or the particular synthetic amphiphile employed. When the structure is that shown as Formula V herein, administration of the compound to plant growth media in which *Arabidopsis thaliana* is grown achieves high inhibition of primary root development (in other words, increases lateral root density) at concentrations up to 50 μM.

In certain embodiments described anywhere herein, the roots of the plant are contacted with a composition comprising the synthetic amphiphiles and/or synthetic anion transporters, for example when inducing alteration in root morphology is desired. In certain embodiments described anywhere herein, the leaves and/or stem of the plant are contacted with a composition comprising the synthetic amphiphiles and/or synthetic anion transporters, for example, when used as an herbicide.

Although synthetic amphiphiles are effective in promoting lateral root growth at lower concentrations they also diminish the growth of the primary roots at higher concentrations and eventually reach toxic concentrations. The concentration ranges of the synthetic amphiphiles for promoting lateral root growth in plants can vary depending on the plant species and/or the particular synthetic amphiphiles employed. Furthermore, in another aspect, a composite having a high concentration of synthetic amphiphiles can be employed as a herbicide for undesired plants, such as by spraying such composite onto the leaves of growing plants.

The synthetic amphiphiles (all three types having Formulas I, II, and III) and the synthetic anion transporters exemplified by, but not limited to, compound numbers 4-24 can be added to the growth solution by any route, protocol, means, etc., appropriate for its administration and embodiments are not limited to any particular route, protocol, means, etc. of addition. Likewise, the lariat ethers or hydraphiles can be added to plant growth media having various compositions. All types of plant growth solution/media can be adopted. A representative plant growth media is an aqueous solution containing $K_3PO_4$, $KNO_3$, $MgSO_4$, $Ca(NO_3)_2$, ferric EDTA (1000×), and micronutrients (1000×). A typical pH of the plant nutrient medium is 5.5.

Figure 5:
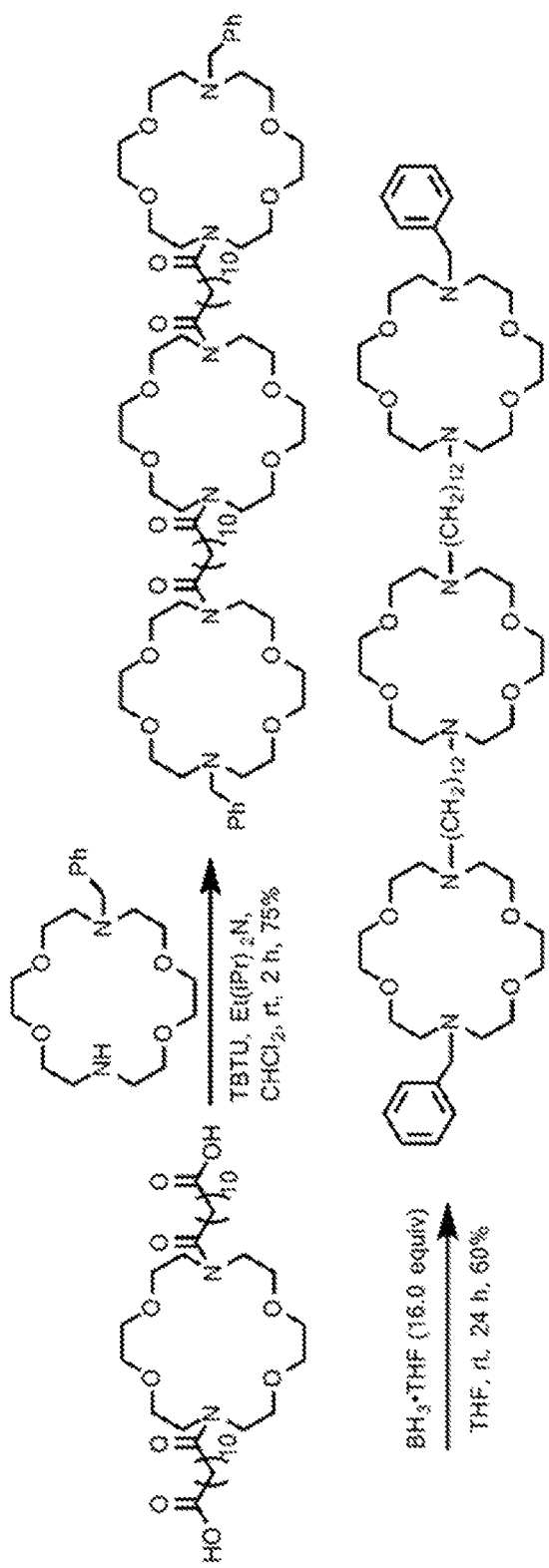
FIG. 5 is a representative synthetic scheme for the preparation of $C_{12}$ benzyl hydraphile.

Disclosed herein are also methods of synthesis for amphiphiles. FIG. 5 illustrates an exemplary synthetic scheme for hydraphiles (Formula I). FIG. 6 is an illustrative example for the synthesis of the chemical structures of N,N'-bis(n-octyl)-4,13-diaza-18-crown-6 (Formula II) and N,N'-bis(2-oxo-n-octyl)-4,13-diaza-18-crown-6 (Formula III).

The following examples of specific aspects are offered for illustrative purposes only, and are not intended to limit the scope of the present disclosure in any way.

EXAMPLES

Example 1. Preparation of Plant Nutrient Media (PN)

Plant Nutrient Media (PN).

To make 500 mL PN media, 485 mL doubly distilled ("dd") $H_2O$ was first added to an autoclave beaker. The following salts and nutrients were added to a beaker and mixed well: 5 mL of 250 mM of $KPO_4$ (pH 5.5), 2.5 mL of 1M $KNO_3$, 1 mL of 1M $MgSO_4$, 1 mL of 1M $Ca(NO_3)_2$, 0.5 mL of Ferric EDTA (1000× or 49 mM) and 0.5 mL of Micronutrients (1000×). In a 1 L autoclaved bottle, 0.6% (3 g) of bacteriological agar was added, followed by 500 mL solution prepared above. The media was autoclaved using the Liquid-30 program.

Micronutrients (1000×) contained 70 mM $H_3BO_3$, 14 mM $MnCl_2.4H_2O$, 0.5 mM $CuSO_4.5H_2O$, 1 mM $ZnSO_4.7H_2O$, 0.2 mM $Na_2MoO_4$, 10 mM NaCl, and 0.01 mM $COCl_2.6H_2O$.

Pouring Plates.

Plant Nutrient Media Plus Sucrose (PNS).

PNS plates were used for plating sterile *Arabidopsis thaliana* (Columbia-0) seeds. A sterile stock of PNS agar was maintained. Sterile sucrose was added to PN media to make PNS media. To make PNS media containing 0.5% sucrose, 5 mL of 50% sucrose (sterile filtered) was added to 500 mL of PN agar and mixed well.

To Make Plates from PNS Stock:

The stored PNS media was liquefied using a water bath and allowed to cool to 55° C. The type of plates, compounds, and concentrations to be used were confirmed while the media cooled. The plates were labeled on the cover and the bottom with all the relevant information. 50 mL sterile centrifuge tubes were used to measure 29,940 μL (29.94 mL) PNS media. A fresh sterile 50 mL tube was used for each plate. The desired amount and concentration of compound was added to the PNS media, mixed by inverting the tube and poured in the plate. Total volume of media and compound in each plate was kept constant at 30 mL. A maximum of 60 μL (0.2% by volume) compound was added per plate. For example: 60 μL of 25 mM compound was added to 29.94 mL PNS media to get final concentration of 50 μM compound in PNS media. Plates were incubated at room temperature for 2 hours before plating seeds on them.

Sterilizing and Plating *A. thaliana* Seeds.

Hands and bench area were washed thoroughly before beginning. Sterilizing solution was prepared in a sterile 15 mL centrifuge tube, by mixing 5 mL of 30% bleach and 5 μL of 10% Triton X-100. *A. thaliana* Col-0 seeds were added to sterile 1.5 mL micro-centrifuge tube. 500 μL of sterilizing solution (30% bleach+0.01% Triton X-100) was added to the seeds, vortexed for 3 seconds and incubated at room temperature for 8 minutes. After 8 minutes, bleach was removed and 1 mL autoclaved MilliQ water was added. Seeds were briefly vortexed, allowed to settle, and the water was removed. The seeds were washed two more times with autoclaved MilliQ water. Seeds were finally suspended in 200 μL of sterile 0.1% agar. These seeds were plated (>20 seeds per plate) on PNS media using sterilized Pasteur pipettes. Seeds were not allowed to touch each other or the boundaries of the plates. The plates were covered with the lid and sealed with surgical tape. Plates were placed in the Intellus Environment Controller, under continuous white light at 23° C. for 11 days.

Measuring Root and Collecting Data.

*A. thaliana* Col-0 seeds (>20 in each trial), the most common strain of this plant, were sterilized and plated on plant nutrient and 0.5% sucrose (PNS) media, containing 0.6% agar. Reference to this type of media can be found in Haughn, G. W., Somerville, C., Sulfonylurea-resistant mutants of *Arabidopsis thaliana*. *Molecular and General Genetics*, 1986, 204(3), 430-434 and Gamborg, O. L., Murashige, T. Thorpe, T. A., Vasil, I. K., Plant tissue culture media. *In Vitro* 1976, 12(7), 473-478. The plates were incubated using an Intellus Environment Controller, under continuous white light at 23° C. for 11 days. At 11 days, the agar around each plant was disturbed and the plant was pulled out from the agar, using sterile forceps. The length of primary roots for each plant was measured (data reported in millimeters) using a ruler. The plant was then transferred to a petri dish containing water, under a dissecting microscope. All the lateral roots, including emerging and developed roots were counted. The number of lateral roots, emerging from the primary root was counted under a dissecting microscope.

Example 2. Measuring Germinated Col-0 Seeds

*A. thaliana* Col-0 seeds (>20 in each trial), the most common strain of this plant, were sterilized and plated on plant nutrient and 0.5% sucrose (PNS) media, containing 0.6% agar. The plates were incubated using an Intellus Environment Controller, under continuous white light at 23° C. The number of seeds germinated were observed under dissecting microscope and counted. Results were recorded every 12 hours for 3 days. The plates were returned to the incubator for root development.

Example 3

N,N'-Dioctanoyl-4,13-diaza-18-crown-6. This compound was prepared by methods known in the art. To a mixture of 4,13-diaza-18-crown-6 (1.2 g, 4.6 mmol) and $Na_2CO_3$ (1.4 g, 13 mmol) in benzene (35 mL) was added octanoyl chloride (1.6 g, 9.8 mmol) in benzene (25 mL) over 30 min and then stirred ambient temperature for an additional 16 h. The mixture was filtered and the solvent evaporated in vacuo. The lariat ether amide was obtained crystallization from hexanes in 71% yield as a white solid (mp 54.5-55° C.).

Example 4

N,N'-Di-n-octyl-4,13-diaza-18-crown-6. This compound was prepared by methods known in the art. 4,13-Diaza-18-crown-6 was acylated with octanoyl and the diamide was reduced with $BH_3$.THF. Short path distillation afforded the lariat ether (63%) as a colorless oil (bp 181-190° C., 0.04 torr).

Example 5

N,N'-Didecanoyl-4,13-diaza-18-crown-6 was synthesized by a method known in the art and as described above in described in Example 3 above using decanoyl chloride. The lariat ether amide was obtained (2.48 g, 100%) as a white solid (mp 65.5-67° C.).

Example 6

N,N'-Didecyl-4,13-diaza-18-crown-6. To a stirred solution of $BH_3$·THF (16 mL, 1.0 M) was added the diamide of Example 5 (1.2 g, 2.1 mmol). The reaction was heated at reflux (24 h) and then quenched by dropwise addition of 6.0 M HCl. The reaction was heated for an additional 3 h, cooled, the pH was adjusted 10 with NaOH pellets, and the product extracted with $CHCl_3$. The organics were was dried with $MgSO_4$ and concentrated in vacuo. Bulb-to-bulb distillation (bp 205-215° C./0.07 mm) afforded the lariat ether in 96% yield as a colorless solid, mp 34.5-36.5° C.

Example 7

Synthesis of $C_{10}$ Benzyl Hydraphile.

$PhCH_2OCO(CH_2)_8COOH$ (decanedioic acid monobenzyl ester). This compound was prepared similarly to $PhCH_2OCO(CH_2)_6COOH$. Dodecanedioic acid (2.90 g, 14.3 mmol), 10% KOH (0.85 g, 15.1 mmol) in MeOH, $Bu_4NBr$ (0.48 g, 1.49 mmol), and $PhCH_2Br$ (2.47 mL, 20.8 mmol) afforded a white solid (2.76 g, 66%).

$PhCH_2OCO(CH_2)_8CO<N18N>CO(CH_2)_8CO_2CH_2Ph$. This compound was prepared similarly to $PhCH_2OCO(CH_2)_6CO<N18N>CO(CH_2)_6CO_2CH_2Ph$. Decanedioic acid monobenzyl ester (2.23 g, 7.62 mmol), HBTU (2.89 g, 7.62 mmol), $Et(i-Pr)_2N$ (7.85 mL, 45.1 mmol), and diaza-18-crown-6 (0.900 g, 3.43 mmol) afforded a colorless oil (2.50 g, 90%). $^1$H-NMR: 0.99 (16H, bs), 1.31 (8H, bs), 2.03 (8H, m), 3.18-3.36 (24H, m), 6.89-7.07 (10H, m). $^{13}$C-NMR: 24.11, 24.49, 28.22, 28.32, 28.50, 28.53, 32.19, 33.33, 37.73, 46.21, 46.29, 48.03, 48.11, 65.02, 68.94, 69.07, 69.32, 69.63, 69.77, 69.91, 70.04, 127.27, 127.69, 135.49, 172.25, 172.27, 172.39.

$HO_2C(CH_2)_8CO<N18N>CO(CH_2)_8CO_2H$. This compound was prepared similarly to $HO_2C(CH_2)_6CO<N18N>CO(CH_2)_6CO_2H$. $PhCH_2OCO(CH_2)_8CO<N18N>CO(CH_2)_8CO_2CH_2Ph$ (2.70 g, 3.33 mmol) and Pd/C (80 mg, 10% activated Pd/C) afforded an off-white solid (2.05 g, 98%, mp=78.9-80.9° C.). $^1$H-NMR: 1.03 (16H, bs), 1.33 (8H, bs), 1.60-2.16 (8H, m), 3.35 (24H, bs). $^{13}$C-NMR: 13.73, 24.32, 24.77, 28.45, 28.50, 28.72, 32.43, 33.53, 33.67, 46.61, 48.39, 48.48, 59.54, 69.00, 69.19, 69.45, 69.55, 69.82, 69.95, 70.17, 70.28, 173.17, 175.91.

$PhCH_2<N18N>CO(CH_2)_8CO<N18N>CO(CH_2)_8CO<N18N>CH_2Ph$. This compound was prepared similarly to $PhCH_2<N18N>CO(CH_2)_6CO<N18N>CO(CH_2)_6CO<N18N>CH_2Ph$. $HCH_2OCO(CH_2)_8CO<N18N>CO(CH_2)_8CO_2CH_2H$ (1.99 g, 3.15 mmol), HBTU (2.59 g, 6.83 mmol), $Et(i-Pr)_2N$ (3.30 mL, 18.9 mmol), and monobenzyl-diaza-18-crown-6 (2.57 g, 7.29 mmol) afford a colorless oil (1.59 g, 41%). $^1$H-NMR: 1.19 (16H, bs), 1.49 (8H, bs), 2.14-2.21 (8H, m), 2.64-2.72 (8H, m), 3.32-3.60 (68H, m), 7.05-7.26 (10H, m). $^{13}$C-NMR: 25.14, 29.16, 29.23, 32.92, 46.73, 48.63, 53.61, 59.73, 69.44, 69.51, 69.80, 69.90, 69.98, 70.05, 70.25, 70.36, 70.39, 70.49, 70.70, 70.77, 126.71, 127.99, 128.6475, 139.25, 173.06, 173.10.

PhCH$_2$<N18N>(CH$_2$)$_{10}$<N18N>(CH$_2$)$_{10}$<N18N> CH$_2$Ph. BH$_3$.THF (15.1 mL, 15.1 mmol, 1 M in THF) and PhCH$_2$<N18N>CO(CH$_2$)$_8$CO<N18N>CO(CH$_2$)$_8$CO <N18N>CH$_2$Ph (1.23 g, 0.946 mmol) afforded a colorless oil (0.62 g, 53%). The spectroscopic properties were identical to those published in Murray, C. L.; Gokel, G. W.; Spacer chain length dependence in hydraphile channels: Implications for channel position within phospholipid bilayers. *Journal of Supramolecular Chemistry* 2001, 1(1), 23-30.

Example 8

PhCH$_2$<N18N>(CH$_2$)$_{10}$<N18N>(CH$_2$)$_{10}$<N18N> CH$_2$Ph. (Dodecyl spacer benzyl hydraphile) Br(CH$_2$)$_{12}$ <N18N>CH$_2$Ph prepared by reacting 1,12-dibromododecane (0.55 g, 1.7 mmol), monobenzyldiaza-18-crown-6 (0.53 g, 1.5 mmol), and Et(i-Pr)$_2$N (0.42 mL, 2.3 mmol) to afford a yellow oil (0.32 g, 35%).

PhCH$_2$<N18N>(CH$_2$)$_{12}$<N18N>(CH$_2$)$_{12}$<N18N>CH$_2$Ph was prepared by reacting Br(CH$_2$)$_{12}$<N18N>CH$_2$Ph (0.42 g, 0.70 mmol), diaza-18-crown-6 (0.086 g, 0.33 mmol), and Et(i-Pr)$_2$N (0.20 mL, 1.1 mmol) to afford the dodecyl hydraphile as an off white solid (0.22 g, 55%).

Further disclosed are methods of synthesis for the above mentioned amphiphiles. FIG. 11, for example, illustrates a synthetic chemical scheme for one of the SAT compounds whose general form is illustrated in Formula IV.

Example 9

General Procedure 1.

A solution of di-n-alkylamine (1.0 equiv.) and diglycolic anhydride (1.1 equiv.) was refluxed in THF (15 mL g$^{-1}$) for 48 h. The solvent was evaporated and the crude product was dissolved in CHCl$_3$, washed with 10% aq. HCl, and the organic layer was evaporated to dryness. The residue was recrystallized from diethyl ether to give Alk$_2$-[DGA]OH.

General Procedure 2.

To a 0° C. solution of RCOOH (1.0 equiv.) in CH$_2$Cl$_2$ (30 mL g$^1$) were added 1-(3-dimethylaminopropyl)-3-ethyl carbodiimide hydrochloride (EDCI, 1.1 equiv.), 1-hydroxybenzotriazole (HOBT, 1.1 equiv.), H$_2$N—R$_2$ tosylate or hydrochloride (1.0 equiv.) and Et$_3$N (2 equiv.). After stirring at room temperature (rt) for 48 h, the reaction was washed with 5% aq. citric acid (20 mL), 5% aq. NaHCO$_3$ (20 mL) and H$_2$O (20 mL). The organic phase was dried (MgSO$_4$), evaporated, and the residue was crystallized or chromatographed over silica gel to give RCONHR$_2$.

General Procedure 3.

RCOOCH$_2$Ph (1.0 equiv.) in EtOH (30 mL g$^{-1}$), 10% Pd/C (0.1 g per g of RCOOCH$_2$Ph) was shaken under 60 psi H$_2$ pressure for 3 h in a Parr apparatus. Filtration of the hot mixture through a celite pad and evaporation of the solvent gave a product that was used in the next step without further purification.

Example 10

18$_2$-[DGA]-GGGPGGG-OH. General procedure 3. Quantities used: 18$_2$-[DGA]-GGGPGGG-OCH$_2$Ph (1.0 g, 0.9 mmol). Product: white solid (0.87 g, 94%), mp 167° C. dec. $^1$H NMR: 0.84 (6H, t, J=6.9 Hz, CH$_3$), 1.22 (60H, m, CH$_3$(CH$_2$)$_{15}$ CH$_3$(CH$_2$)$_{16}$CH$_2$N), 3.26 (2H, t, J=7.5 Hz, CH$_3$(CH$_2$)$_{16}$ CH$_2$N), 3.00-4.40 (19H, Pro NCH$_2$CH$_2$CH$_2$, GlyCH$_2$, CO—CH$_2$O, Pro CH), 7.28 (1H, NH), 7.50 (1H, t, J=6.0 Hz, NH), 7.69 (1H, t, J=6.0 Hz, NH), 7.90-8.05 (2H, m, NH), 8.32 (1H, bs, NH). $^{13}$C NMR: 14.1, 22.7, 25.1, 26.9, 27.1, 27.6, 28.8, 29.3, 29.4, 29.6, 29.7, 31.9, 41.6, 41.9, 42.6, 42.8, 43.4, 46.4, 47.0, 61.2, 69.0, 70.9, 168.6, 168.9, 170.4, 70.8, 171.0, 171.3, 172.6, 173.7. IR (CHCl$_3$): cm$^{-1}$ 3306, 3083, 2918, 2850, 1730, 1658, 1651, 1646, 1540, 1467, 1412, 1378, 1338, 1241, 1130, 1030, 909, 722. Anal. Calcd. For C$_{64}$H$_{118}$N$_8$O$_{11}$. H$_2$O: C, 64.40, H, 10.13, N, 9.39. Found: C, 64.36, H, 10.11, N, 9.21%.

[CH$_3$(CH$_2$)$_{17}$]$_2$NCOCH$_2$OCH$_2$CO-Gly-Gly-Gly-Pro-Gly-Gly-Gly-O(CH$_2$)$_6$CH$_3$, Compound 9.

TsOH.GGG-OC$_7$H$_{15}$. GGG (2.0 g, 10.6 mmol) and p-TsOH H$_2$O (2.2 g, 11.6 mmol) were added to 1-heptanol (12 g, 103.3 mmol) and PhMe (40 mL). The mixture was heated to reflux and water was removed azeotropically (Dean-Stark trap, h). The mixture was cooled (rt), evaporated, and crystallized from CH$_3$OH:Et$_2$O (20 mL:60 mL) to give 4.32 g (89%) of a white solid, mp 149-150° C. $^1$H NMR (CD$_3$OD): 0.91 (3H, t, J=7.2 Hz, CH$_3$(CH$_2$)$_4$CH$_2$CH$_2$O), 1.32 (8H, m, CH$_3$(CH$_2$)$_4$CH$_2$CH$_2$O), 1.64 (2H, bs, CH$_3$ (CH$_2$)$_4$CH$_2$CH$_2$O), 2.37 (3H, s, Ar—CH$_3$), 3.65-3.75 (2H, m, GlyCH$_2$), 3.93 (2H, s, GlyCH$_2$), 3.98 (2H, s, GlyCH$_2$), 4.11 (2H, t, J=6.6 Hz, CH$_3$(CH$_2$)$_4$CH$_2$CH$_2$O), 7.24 (2H, d, J=8.1 Hz, Ar—H), 7.71 (2H, d, J=8.1 Hz, Ar—H). $^{13}$C NMR (CD$_3$OD): 14.5, 21.4, 23.8, 27.0, 29.8, 30.2, 33.0, 41.7, 42.1, 43.2, 66.6, 127.1, 130.0, 141.9, 143.6, 168.1, 171.4, 171.9. IR (nujol): cm$^{-1}$ 3336, 3263, 3110, 2922, 2853, 2719, 1740, 1706, 1685, 1651, 1594, 1547, 1499, 1461, 1412, 1377, 1368, 1313, 1232, 1214, 1175, 1128, 1037, 1014, 912, 816, 738, 724, 684.

Cbz-PGGG-OC$_7$H$_{15}$. Quantities used: Cbz-L-Proline (1.08 g, 4.3 mmol) and TsOH GGG-OC$_7$H$_{15}$ (2.0 g, 4.4 mmol). The crude product was chromatographed (silica gel, CH$_3$OH:CHCl$_3$ 98:2-95:5) to give colorless crystals (2.01 g, 90%), mp 94-96° C. $^1$H NMR: 0.87 (3H, t, J=6.9 Hz, CH$_3$(CH$_2$)$_4$CH$_2$CH$_2$O), 1.27 (8H, m, CH$_3$(CH$_2$)$_4$ CH$_2$CH$_2$O), 1.60 (2H, bs, CH$_3$(CH$_2$)$_4$CH$_2$CH$_2$O), 1.75-2.20 (4H, m, Pro NCH$_2$CH$_2$CH$_2$), 3.45-3.60 (2H, m, Pro NCH$_2$CH$_2$CH$_2$), 3.75-4.00 (6H, GlyCH$_2$), 4.07 (2H, t, J=6.6 Hz, CH$_3$(CH$_2$)$_4$CH$_2$CH$_2$O), 4.24 (1H, t, J=6.3 Hz, Pro CH), 5.02-5.17 (2H, m, PhCH 7.33 (5H, m, Ar—H), 7.68 (1H, bs, NH). $^{13}$C NMR: 14.0, 22.5, 25.7, 28.5, 28.8, 29.5, 31.6, 41.2, 43.0, 43.4, 47.1, 61.0, 65.5, 67.6, 127.8, 128.2, 128.5, 136.2, 156.0, 169.4, 169.7, 171.7, 173.3. IR (CHCl$_3$): cm$^{-1}$ 3310, 3068, 2955, 2931, 2858, 1749, 1669, 1541, 1419, 1360, 1206, 1125, 1091, 1030, 986, 919, 770, 731, 698.

PGGG-OC$_7$H$_{15}$. General procedure 3. Quantities used: Cbz-PGGG-OC$_7$H$_{15}$ (1.0 g, 1.9 mmol). Product: a white, waxy solid $^1$H NMR (CD$_3$OD): 0.91 (3H, t, J=7.2 Hz, (0.74 g, 100%). CH$_3$(CH$_2$)$_4$CH$_2$CH$_2$O), 1.32 (8H, m, CH$_3$(CH$_2$)$_4$ CH$_2$CH$_2$O), 1.65 (2H, bs, CH$_3$(CH$_2$)$_4$CH$_2$CH$_2$O), 1.75-2.20 (4H, m, ProNCH$_2$CH$_2$CH$_2$), 2.70-3.00 (2H, m, Pro NCH$_2$CH$_2$CH$_2$), 3.70-4.05 (7H, GlyCH$_2$, Pro CH), 4.13 (2H, t, J=6.6 Hz, CH$_3$(CH$_2$)$_4$CH$_2$CH$_2$O). $^{13}$C NMR (CD$_3$OD): 14.5, 22.3, 23.8, 26.1, 26.8, 27.0, 27.1, 27.4, 29.8, 30.2, 31.9, 33.0, 42.1, 43.5, 43.7, 43.8, 61.7, 64.3, 66.5, 171.0, 171.4, 172.0, 178.2. IR (cm$^{-1}$) 3284, 3177, 2921, 2855, 1740, 1653, 1461, 1377, 1155, 1077, 1029, 967, 892, 846, 770, 723.

18$_2$-[DGA]-GGGPGGG-OC$_7$H$_{15}$. General procedure 2. Quantities used: 18$_2$-[DGA]-GGG-OH (0.16 g, 0.2 mmol) and PGGG-OC$_7$H$_{15}$ (0.08 g, 0.2 mmol). Crude product was chromatographed (silica gel, CH$_3$OH:CHCl$_3$ 9:1-85:15) to give a white solid (0.14 g, 61%), mp 99-101° C. $^1$H NMR:

0.85-0.90 (9H, $CH_3(CH_2)_{15}CH_2CH_2N$, $CH_3(CH_2)_4CH_2CH_2O$), 1.24 (68H, m, $CH_3(CH_2)_{15}CH_2CH_2N$, $CH_3(CH_2)_4CH_2CH_2O$), 1.49 (4H, bs, $CH_3(CH_2)_{15}CH_2CH_2N$), 1.60 (2H, bs, $CH_3(CH_2)_4CH_2CH_2O$), 1.80-2.20 (4H, m, ProNCH$_2$CH$_2$CH$_2$), 3.05 (2H, t, J=7.5 Hz, $CH_3(CH_2)_{15}CH_2CH_2N$), 3.24 (2H, t, J=7.5 Hz, $CH_3(CH_2)_{15}CH_2CH_2N$), 3.45-3.75 (2H, m, Pro NCH$_2$CH$_2$CH$_2$), 3.85-4.10 (16H, GlyCH$_2$, $CH_3(CH_2)_4CH_2CH_2O$, COCH$_2$O), 4.27 (2H, s, COCH$_2$O), 4.36 (1H, t, J=6.6 Hz, Pro CH), 7.65 (2H, bs, NH), 7.89 (1H, bs, NH), 8.03 (1H, bs, NH), 8.26 (1H, bs, NH), 8.42 (1H, bs, NH). $^{13}$C NMR: 14.0, 14.1, 22.6, 22.7, 25.1, 25.8, 26.9, 27.1, 27.6, 28.5, 28.8, 28.9, 29.1, 29.3, 29.4, 29.5, 29.6, 29.7, 31.7, 31.9, 41.2, 42.0, 42.8, 42.9, 43.4, 46.3, 61.3, 65.6, 69.4, 71.2, 168.5, 168.9, 170.2, 170.3, 170.4, 170.7, 171.2, 173.3. IR (CHCl$_3$): cm$^{-1}$ 3308, 2920, 2851, 1744, 1652, 1540, 1467, 1376, 1338, 1209, 1129, 1109, 1031, 722. Anal. Calcd. for $C_{64}H_{118}N_8O_{11}H_2O$: C, 64.40, H, 10.13, N, 9.39. Found: C, 64.36, H, 10.11, N, 9.21%.

Example 11

Boc-PGGG-OCH$_2$Ph.

Boc-L-Proline (1.43 g, 6.7 mmol), TsOH GGG-O—CH$_2$Ph (3.0 g, 6.7 mmol), and Et$_3$N (2.80 mL) were dissolved in CH$_2$Cl$_2$ (40 mL) and cooled to 5° C. EDCI (1.34 g, 7 mmol) was added and reaction was stirred at ambient temperature for 3 days. Solvent was evaporated and residue was dissolved in EtOAc (50 mL) and washed with saturated aqueous NH$_4$Cl (25 mL) and brine (25 mL), dried over MgSO$_4$ and evaporated. The crude, oily product was purified by chromatography (SiO$_2$, 5% MeOH—CH$_2$Cl$_2$) and afforded colorless crystals (2.25 g, 71%, mp 54-55 C). $^1$H-NMR CDCl$_3$: 1.42 (9H, s, C(CH$_3$)$_3$), 1.80-2.20 (4H, m, ProNCH$_2$CH$_2$CH$_2$), 3.35-3.55 (2H, m, ProNCH$_2$CH$_2$CH$_2$), 3.85-4.20 (7H, m, GlyNCH$_2$, ProNCH), 5.15 (2H, s, PHCH$_2$O), 7.05 (2H, bs, GlyCONH), 7.30-7.35 (5H, m, H$_{Ar}$), 7.80 (1H, bs, GlyCONH). $^{13}$C-NMR: 24.6, 28.3, 29.4, 41.1, 43.0, 43.3, 47.2, 60.7, 66.9, 80.9, 128.4, 128.5, 128.7, 135.4, 155.8, 169.6, 170.0, 173.9. IR (KBr): 3310, 3066, 2976, 2933, 1753, 1667, 1540, 1455, 1408, 1366, 1245, 1174, 1129, 1031, 974, 912, 773, 739, 698. Anal. $C_{48}H_{78}N_8O_{11}$: C, 61.12; H, 8.34; N, 11.88%. Found: C, 60.87; H, 8.26; N, 11.65%.

N,N-Dioctadecyl 3-oxaglutaramide (18$_2$DGA) A solution of dioctadecylamine (2.0 g, 3.8 mmol) and diglycolic anhydride (0.44 g, 3.8 mmol) in toluene (50 mL) was refluxed for 48 h. The solvent was evaporated and the crude product crystallized from CHCl$_3$ to give a white solid (2.12 g, 87%), mp 80-81° C. $^1$H-NMR CDCl$_3$: 0.87 (6H, t, J=6.9 Hz, CH$_2$CH$_3$), 1.25 (60H, pseudo-s, $CH_3(CH_2)_{15}CH_2CH_2N$), 1.55 (4H, bs, $CH_3(CH_2)_{15}CH_2CH_2N$), 3.07 (2H, t, J=7.8 Hz, $CH_3(CH_2)_{16}CH_2N$), 3.34 (2H, t, J=7.8 Hz, $CH_3(CH_2)_{16}$—CH$_2$N), 4.21 (2H, s, COCH$_2$O), 4.38 (2H, s, COCH$_2$O). $^{13}$C-NMR: 14.2, 22.8, 26.9, 27.0, 27.5, 28.7, 29.4, 29.5, 29.6, 29.7, 29.8, 32.0, 47.0, 71.4, 73.2, 171.0, 172.2. IR (KBr): 2918, 2850, 1748, 1602, 1488, 1472, 1463, 1431, 1356, 1224, 1159, 1135, 1045, 1013, 990, 920, 885, 729, 720, 689, 643 cm$^{-1}$.

18$_2$DGA-GGG-OCH$_2$Ph.

To 18$_2$DGA-OH (1 g, 1.5 mmol) dissolved in CH$_2$Cl$_2$ (30 mL), 1-(3-dimethylaminopropyl)-3-ethylcarbodiimide hydrochloride (0.31 g, 1.6 mmol) was added and the mixture was stirred at room temperature. After 0.5 h, TsOH H$_2$N-GGG-OCH$_2$Ph (0.66 g, 1.5 mmol) and Et$_3$N (0.6 mL) were added and the mixture was stirred at ambient temperature overnight. The reaction mixture was successively washed with water (20 mL), 0.5 M HCl (20 mL), water (20 mL), 10% Na$_2$CO$_3$ (20 mL), and brine (20 mL), dried (MgSO$_4$), evaporated and the residue crystallized from MeOH to afford a white solid (1.26 g, 89%), mp 41-42 C. $^1$H-NMR CDCl$_3$: 0.86 (6H, t, J=6.9 Hz, CH$_2$CH$_3$), 1.24 (60H, pseudo-s, $CH_3(CH_2)_{15}CH_2CH_2N$), 1.49 (4H, bs, $CH_3(CH_2)_{15}CH_2CH_2N$), 1.61 (1H, H$_2$O), 3.04 (2H, t, J=7.5 Hz, $CH_3(CH_2)_{16}CH_2N$), 3.24 (2H, t, J=7.5 Hz, $CH_3(CH_2)_{16}CH_2N$), 3.95-4.05 (6H, m, GlyNCH$_2$), 4.09 (2H, s, COCH$_2$O), 4.29 (2H, s, COCH$_2$O), 5.12 (2H, s, PHCH$_2$O), 7.23 (1H, t, J=6.0 Hz, GlyCONH), 7.30-7.35 (5H, m, HAr), 7.93 (1H, t, J=5.7 Hz, GlyCONH), 8.27 (1H, t, J=5.7 Hz, GlyCONH). $^{13}$C-NMR: 13.9, 22.5, 26.7, 26.9, 27.4, 28.6, 29.2, 29.3, 29.6, 31.8, 41.0, 42.9, 46.3, 46.7, 66.9, 69.6, 71.7, 128.2, 128.4, 128.6, 135.3, 168.6, 169.7, 169.8, 170.0, 171.5. IR (KBr): 3293, 2916, 2849, 1749, 1651, 1544, 1467, 1196, 1128, 1031, 721, 697 cm$^{-1}$. Anal. Calcd for $C_{53}H_{94}N_4O_7$+0.5 H$_2$O: C, 70.11; H, 10.54; N, 6.17%. Found: C, 70.18; H, 10.55; N, 6.18%.

18$_2$DGA-GGG-OH.

18$_2$DGA-GGG-OCH$_2$Ph (1.0 g, 1.1 mmol) was dissolved in absolute ethanol (100 mL) and 10% Pd/C (0.2 g) was added and this mixture was shaken under 60 psi H$_2$ for 3 h. The reaction mixture was heated to reflux and filtered hot through a celite pad. The solvent was evaporated under reduced pressure to afford a white solid (0.86 g, 96%), mp 163-164 C. $^1$H-NMR CD$_3$OD: 0.90 (6H, t, J=6.9 Hz, CH$_2$CH$_3$), 1.29 (60H, pseudo-s, $CH_3(CH_2)_{15}CH_2CH_2N$), 1.57 (4H, bs, $CH_3(CH_2)_{15}$—CH$_2$CH$_2$N), 3.21 (2H, t, J=7.8 Hz, $CH_3(CH_2)_{16}CH_2N$), 3.35 (2H, t, J=7.8 Hz, $CH_3(CH_2)_{16}CH_2N$), 3.93 (2H, s, GlyNCH$_2$), 3.94 (2H, s, GlyNCH$_2$), 3.97 (2H, s, GlyNCH$_2$), 4.12 (2H, s, COCH$_2$O), 4.40 (2H, s, COCH$_2$O). $^{13}$C-NMR: IR (KBr): 3285, 3084, 2925, 2852, 1740, 1650, 1551, 1467, 1420, 1378, 1219, 1128, 1033, 1011, 721, 681 cm$^{-1}$. Anal. Calcd for $C_{46}H_{88}N_4O_7$: C, 68.28; H, 10.96; N, 6.92%. Found: C, 67.97; H, 10.92; N, 6.81%.

18$_2$DGA-GGGPGGG-OCH$_2$Ph.

18$_2$DGA-GGG-OH (0.31 g, 0.39 mmol) and 1-(3-dimethylaminopropyl)-3-ethylcarbodiimide hydrochloride (0.08 g, 0.42 mmol) were stirred for 0.5 h in CH$_2$Cl$_2$ (40 mL) and HCl.H$_2$N-PGGG-OCH$_2$Ph (0.16 g, 0.39 mmol) in CH$_2$Cl$_2$ (10 mL) containing Et$_3$N (0.15 mL) was added. The mixture was stirred for 48 h at room temperature, solvent was evaporated, and the residue was crystallized from MeOH to give 18$_2$DGA-GGGPGGG-OCH$_2$Ph as a white solid (0.37 g, 82%), mp 116-118 C. $[\alpha]^{20}_D$ 8.9 (c 1.055, CHCl$_3$). $^1$H-NMR CDCl$_3$: 0.87 (6H, t, J=6.9 Hz, CH$_2$CH$_3$), 1.25 (60H, pseudo-s, $CH_3(CH_2)_{15}CH_2CH_2N$), 1.47 (4H, bs, $CH_3(CH_2)_{15}CH_2CH_2N$), 1.80-2.20 (4H, m, ProNCH$_2$CH$_2$CH$_2$), 3.03 (2H, t, J=7.5 Hz, $CH_3(CH_2)_{16}CH_2N$), 3.23 (2H, t, J=7.5 Hz, $CH_3(CH_2)_{16}CH_2N$), 3.40-3.45 (1H, m, ProNCH$_2$CH$_2$CH$_2$), 3.50-3.55 (1H, m, ProNCH$_2$CH$_2$CH$_2$), 3.90-4.05 (12H, m, GlyNCH$_2$), 4.12 (2H, s, COCH$_2$O), 4.26 (2H, s, COCH$_2$O), 4.35 (1H, bs, ProNCH), 5.12 (2H, s, PHCH$_2$O), 7.33 (5H, s, HAr), 7.66 (1H, bs, GlyCONH), 7.76 (1H, br, GlyCONH), 7.85 (1H, br, GlyCONH), 8.06 (1H, bs, GlyCONH), 8.31 (1H, bs, GlyCONH), 8.47 (1H, bs, GlyCONH). $^{13}$C-NMR: 13.9, 22.5, 24.9, 26.8, 26.9, 27.5, 28.6, 29.2, 29.5, 29.6, 31.8, 41.1, 41.8, 42.5, 42.6, 42.8, 43.1, 46.1, 46.7, 61.1, 67.0, 69.1, 70.9, 128.2, 128.4, 128.6, 135.4, 168.5, 169.0, 170.3, 170.5, 170.6, 170.9, 171.2, 173.7. IR (KBr) cm$^{-1}$: 3301, 2922, 2853, 1740, 1653, 1540, 1457, 1242, 1131, 1029, 720. MS (ESI): m/z [M+Na]$^+$ calculated for $C_{64}H_{110}N_8O_{11}$Na 1189, observed 1190. Anal. Calcd for $C_{64}H_{110}N_8O_{11}$: C, 65.83; H, 9.50; N, 9.60%. Found: C, 65.38; H, 9.68; N, 9.16%.

While the invention has been described in connection with specific embodiments thereof, it will be understood that the inventive device is capable of further modifications. This patent application is intended to cover any variations, uses, or adaptations of the invention following, in general, the principles of the invention and including such departures from the present disclosure as come within known or customary practice within the art to which the invention pertains and as can be applied to the essential features herein before set forth.

What is claimed is:

1. A method for increasing the lateral root density of a plant, the method comprising treating one or more plants with a composition comprising a lariat ether amide with the structure of formula III:

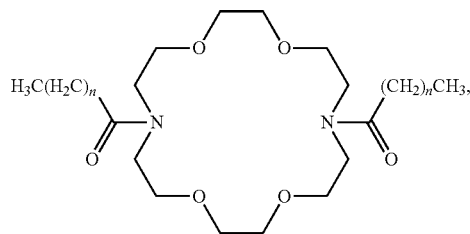

wherein n is 4 to 20, and wherein the increase in the lateral root density of the plant is in comparison to the average lateral root density of a statistically significant control population of plants that has not been treated with the lariat ether amide.

2. The method of claim 1, further comprising selecting a treated plant based on the increase in lateral root density.

3. The method of claim 1, wherein the concentration of the lariat ether amide in the composition is from about 0.01 µM to about 1.0 µM.

4. The method of claim 1, wherein the concentration of the lariat ether amide in the composition is from about 1.0 µM to about 25 µM.

* * * * *